(12) United States Patent
Puchacz et al.

(10) Patent No.: US 9,765,139 B2
(45) Date of Patent: *Sep. 19, 2017

(54) PERFUSION METHOD FOR MANUFACTURING ETANERCEPT

(71) Applicant: Coherus Biosciences, Inc., Redwood City, CA (US)

(72) Inventors: Ela Puchacz, Pleasanton, CA (US); James Russell Grove, Mountain View, CA (US)

(73) Assignee: Coherus Biosciences, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/226,522

(22) Filed: Mar. 26, 2014

(65) Prior Publication Data

US 2014/0296489 A1   Oct. 2, 2014

Related U.S. Application Data

(60) Provisional application No. 61/805,215, filed on Mar. 26, 2013, provisional application No. 61/933,665, filed on Jan. 30, 2014.

(51) Int. Cl.
| | |
|---|---|
| *C12N 15/79* | (2006.01) |
| *C07K 14/715* | (2006.01) |
| *C07K 16/24* | (2006.01) |
| *C07K 14/705* | (2006.01) |
| *C12P 21/02* | (2006.01) |
| *C07K 19/00* | (2006.01) |
| *C12N 5/16* | (2006.01) |
| *C12M 1/00* | (2006.01) |

(52) U.S. Cl.
CPC ...... *C07K 16/241* (2013.01); *C07K 14/70575* (2013.01); *C07K 14/7151* (2013.01); *C12N 15/79* (2013.01); *C12P 21/02* (2013.01); *C07K 2319/00* (2013.01); *C07K 2319/30* (2013.01); *C12M 29/10* (2013.01); *C12N 5/16* (2013.01)

(58) Field of Classification Search
None
See application file for complete search history.

(56) References Cited

U.S. PATENT DOCUMENTS 7,294,481 B1 * 11/2007 Fung ................. C07K 14/525
   435/235.1
2008/0131934 A1 * 6/2008 Crowley ............... C12M 25/10
   435/70.3

* cited by examiner

*Primary Examiner* — Zachary Howard
(74) *Attorney, Agent, or Firm* — Wood, Phillips, Katz, Clark & Mortimer

(57) ABSTRACT

Production of etanercept using perfusion methods achieves attractive yields of properly folded protein. Desired temperature, feed media, titers and percent correctly folded protein are disclosed.

16 Claims, 25 Drawing Sheets
(22 of 25 Drawing Sheet(s) Filed in Color)

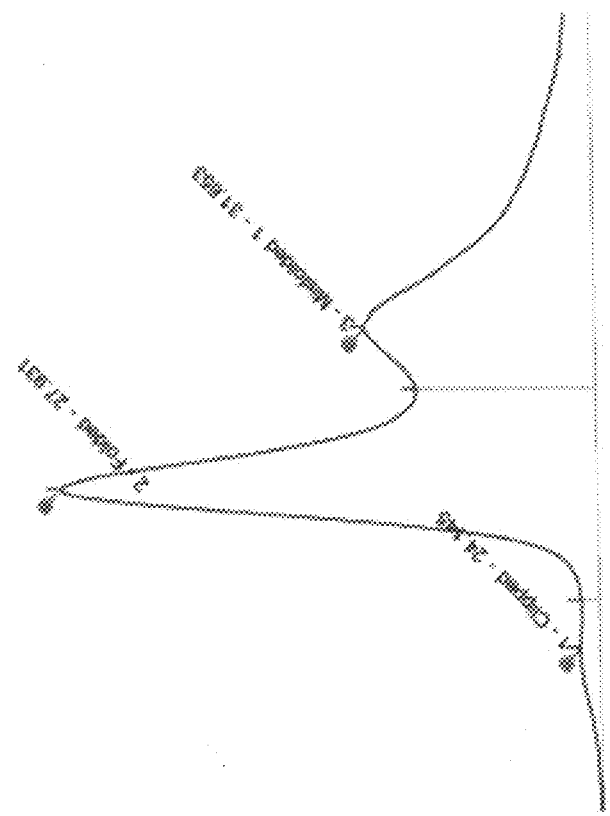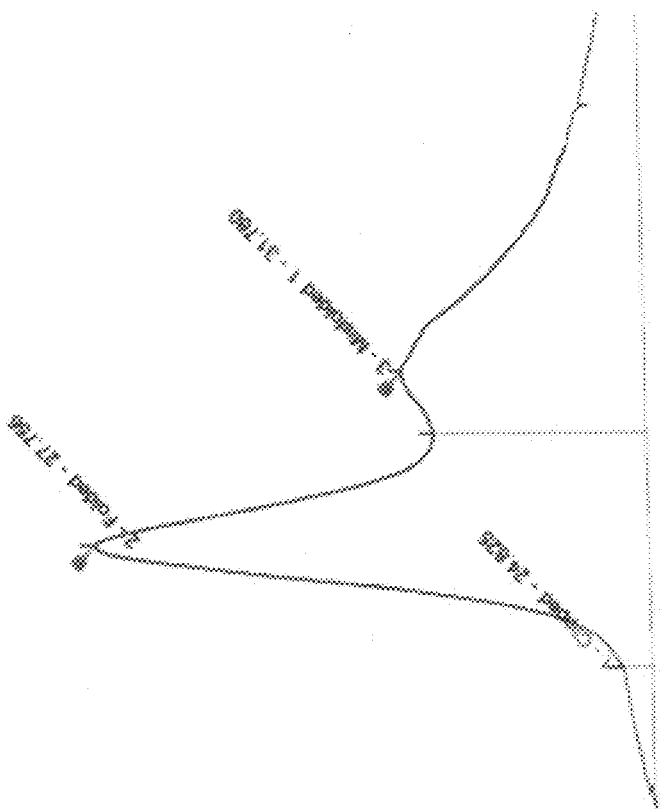
FIGURE 13

IEF Gel for Example 6

PERFUSION METHOD FOR MANUFACTURING ETANERCEPT

FIELD OF THE INVENTION

The present invention relates generally to methods of manufacturing etanercept, and, more particularly, to manufacture of etanercept using perfusion in which cells producing the protein are cultured in the presence of a culture medium that is being continuously or periodically removed from and added to a reaction vessel where the production is taking place. The disclosed method achieves production of correctly folded etanercept in excellent yields having desired glycosylation profiles.

BACKGROUND OF THE INVENTION

A form of etanercept commercially available from Amgen under the trade-name Enbrel® is known to be a dimeric fusion polypeptide consisting of the extracellular ligand-binding portion of the human 75 kilodalton (p75) tumor necrosis factor receptor (TNFR) linked to the Fc portion of human IgG1. It consists of 934 amino acids and has an apparent molecular weight of approximately 150 kilodaltons (Physicians Desk Reference, 2002, Medical Economics Company Inc.) The Fc component of etanercept contains the constant heavy 2 (CH2) domain, the constant heavy 3 (CH3) domain and hinge region, but not the constant heavy 1 (CH1) domain of human IgG1. An Fc domain can contain one or all of the domains described above. Etanercept is usually produced by recombinant DNA technology in a Chinese hamster ovary (CHO) mammalian cell expression system.

People suffering from certain types of inflammatory diseases such as rheumatoid arthritis, plaque psoriasis, psoriatic arthritis, juvenile idiopathic arthritis, and ankylosing spondylitis, have an immune system that over produces tumor necrosis factor ("TNF"). Administration of etanercept has been found effective for treatment of some inflammatory diseases because it can reduce the levels of the active form of TNF in a subject by binding to TNF as a decoy receptor.

Etanercept can be produced in a known manner by recombinant DNA technology in a Chinese hamster ovary ("CHO") mammalian cell expression system. Unfortunately, the product that is produced by the CHO cells contains a large amount of incorrectly or misfolded and/or aggregated etanercept. For pharmaceutical use, it is desirable to provide etanercept that is relatively free of incorrectly folded and aggregated protein because the incorrectly folded/aggregated protein will not have the same therapeutic effect as the correctly folded protein, and may actually be detrimental to the patient. Moreover, the known tendency for manufacture of etanercept to cause aggregates or misfolded protein can significantly reduce yields and increase costs in recombinant processes used to manufacture the protein. Thus, the alleviation of misfolding is not only highly desirable from a therapeutic standpoint, but also from the standpoint of process economics.

TNFR domain of Etanercept contains several cysteines which form disulfide bridges. This bridging contributes to protein assuming certain secondary and tertiary structures (folding). The combination of potential bridge forming increases with the number of available cysteines. Improperly formed cysteine-cysteine bridges result in improper folding thus lower protein activity. Even when misfolding is thought to be negligible during production of pharmaceutical proteins, e.g., in the case of mammalian secretory expression, aggregation and some misfolding may still occur.

Need exists for methods capable of producing properly folded etanercept in commercially attractive yields. Moreover, there exists need for production methods which can operate at temperatures other than those previously thought desirable in the art.

SUMMARY OF THE INVENTION

The invention provides a perfusion method for manufacturing etanercept comprising the following steps: (a) preparing a mixture comprising cells capable of expressing a protein comprising etanercept and a culture medium suitable for conducting such expression; (b) in a suitable vessel containing the mixture, causing the cells to produce the protein comprising etanercept; and (c) periodically or continuously removing spent culture medium from, and adding fresh culture medium to, the reaction vessel. The disclosed method is capable of producing correctly folded etanercept having a glycosylation profile substantially similar to that of commercially available etanercept sold under the tradename Enbrel®. Moreover, the disclosed perfusion method can produce etanercept protein in which correctly folded etanercept comprises greater than 40, 50 or 60 wt. % of the protein.

The medium in which production is carried out preferably comprises SFM4CHO® medium or a mixture of BalanCD™ CHO Growth A and HyClone™ Hycell CHO mediums (most preferably the BalanCD/Hycell medium mixture) and is supplemented with feeds promoting cell growth and productivity, such as glutamine, CHOZN, Feed 1, Feed 2 and Efficient Feed A (such feeds being identified further below). Further supplements present in the culture medium are selected from the group consisting of galactose, dexamethasone and ManNac which are shown to improve culture efficiency including enhancements from the standpoint of generally achieving desired glycosylation profile, which involves, in particular, attaining higher degrees of sialylation in the secreted proteins. In particularly preferred embodiments of the disclosed method, all three of these supplements (galactose, dexamethasone and ManNac) are used.

Cells producing etanercept are present in the vessel at a density of at least 1,000,000 cells/ml, and preferably at a density of at least 5,000,000, and most preferably at least about 10,000,000 cells/ml. Prior to step (a), during a growth phase conducted to increase the number of cells capable of expressing etanercept (before substantial initiation of production phase), such cells capable of expressing a protein comprising etanercept can be grown at a temperature selected from; (i) about 28° C. to about 37° C.; and (ii) preferably about 35° C. to about 36° C. During a subsequent production phase, after the growth phase is substantially completed, the etanercept production is carried out at a temperature selected from (i) greater than about 32° C.; (ii) greater than about 33° C.; (iii) greater than about 34° C.; (iv) greater than about 35° C.; (v) the range of about 33° C. to about 36° C.; (vi) the range of about 35° C. to about 36° C.; (vii) 32.5° C.; (viii) 33.5° C.; (ix) 34.5° C.; and (x) 35.5° C. The method of the invention preferably comprises continuously or periodically, but preferably continuously, harvesting the etanercept during the production thereof. Moreover, the removal of spent medium and replacement with fresh culture medium, i.e., perfusion, occurs preferably continuously. Harvesting of etanercept, present in the continuously withdrawn culture medium, is also preferably carried out continuously.

A particularly preferred perfusion method for producing correctly folded etanercept involves conducting the production phase above 33° C. and between 33° C. to about 36° C., and most preferably at about 33.5° C. using a culture medium comprising the BalanCD/Hycell mixture (approx. 1:1), CHOZN, cottonseed hydrolysate, dexamethasone, galactose and ManNAc. Other feed supplements may be present, such as glutamine, Feed 1, Feed 2, Efficient Feed A and manganese chloride.

The volumetric productivity of the described process and the quality of the produced etanercept can be evaluated by using several methods well known to those skilled in the art. These methods include but are not limited to assays that quantify total and active protein (titers), qualify level of protein sialylation such as the isoelectric focusing (IEF) gels, hydrophobic Interaction chromatography and others.

The invention is further directed to a method for producing etanercept to reduce protein misfolding comprising culturing a recombinant mammalian host cell which encodes a protein comprising etanercept so as to produce such protein, wherein during a production phase, the host cell is cultured using a perfusion process at a temperature selected from (i) greater than about 32° C.; (ii) greater than about 33° C.; (iii) greater than about 34° C.; (iv) greater than about 35° C.; (v) the range of about 33° C. to about 36° C.; (vi) the range of about 35° C. to about 36° C.; (vii) 32.5° C.; (viii) 33.5° C.; (ix) 34.5° C.; and (x) 35.5° C.; to obtain a protein product comprising at least about 40 wt. %, preferably at least about 50 wt. %, and most preferably at least about 60 wt. % of correctly folded etanercept, preferably as determined by HIC chromatography, and such that the total amount of protein product (correctly and incorrectly folded protein) is produced in titers of at least about 0.2 to about 1 g/L. Titers can be measured in a known manner using conventional methods such as the ForteBio method.

In a further embodiment the invention provides a perfusion method for manufacturing correctly folded etanercept comprising the following steps: (a) preparing a mixture comprising cells capable of expressing a protein comprising etanercept and a culture medium suitable for conducting such expression; (b) in a suitable vessel containing the mixture, causing the cells to produce the protein comprising etanercept; and (c) periodically or continuously removing spent culture medium from, and adding fresh culture medium to, the reaction vessel; and wherein: (1) the culture medium comprises BalanCD/Hycell® medium, dexamethasone, galactose and ManNAc; (2) prior to step (a), the cells capable of expressing the protein comprising etanercept are grown in a growth phase at a temperature of 28° C. to 37° C.; (3) production of the protein comprising etanercept is carried out at a temperature of 33° C. to 36° C.; and (4) the protein comprising etanercept comprises at least 40 wt. %, 50 wt. %, or 60 wt. % of correctly folded etanercept, and wherein the total amount of correctly folded and incorrectly folded protein produced during the production phase is produced in titers of about 0.2 to about 1 g/L.

The present invention is further directed to correctly folded etanercept produced by a perfusion method comprising the following steps: (a) preparing a mixture comprising cells capable of expressing a protein comprising etanercept and a culture medium suitable for conducting such expression; (b) in a suitable vessel containing the mixture, causing the cells to produce the protein comprising etanercept; and (c) periodically or continuously removing spent culture medium from, and adding fresh culture medium to, the reaction vessel; and wherein: (1) the culture medium comprises the above referenced BalanCD/Hycell medium mixture, dexamethasone, galactose and ManNAc; (2) prior to step (a), the cells capable of expressing the protein comprising etanercept are grown in a growth phase at a temperature of 28° C. to 37° C.; (3) production of the protein comprising etanercept is carried out at a temperature of 33° C. to 36° C.; and (4) the protein comprising etanercept comprises at least 40 wt. %, 50 wt. %, or 60 wt. % of correctly folded etanercept, and wherein the total amount of correctly folded and incorrectly folded protein produced during the production phase is produced in titers of about 0.2 to about 1 g/L.

A further embodiment of the invention is a perfusion method for producing correctly folded etanercept having a glycosylation profile substantially similar to that of commercially available etanercept sold under the tradename Enbrel®, said method comprising the steps of: (a) preparing a mixture comprising cells capable of expressing a protein comprising etanercept and a culture medium suitable for conducting such expression; (b) in a suitable vessel containing the mixture, causing the cells to produce the protein comprising etanercept; and (c) periodically or continuously removing spent culture medium from, and adding fresh culture medium to, the reaction vessel; wherein dexamethasone, galactose and ManNAc are present in the culture medium to achieve said substantially matching glycosylation profile. In a further preferred embodiment, the additional inclusion of cottonseed hydroysates is found to further enhance the glycoprofile.

Another embodiment of the invention is a perfusion method for producing correctly folded etanercept having a glycosylation profile substantially similar to that of commercially available etanercept sold under the tradename Enbrel®, said method comprising the steps of: (a) preparing a mixture comprising cells capable of expressing a protein comprising etanercept and a culture medium suitable for conducting such expression; (b) in a suitable vessel containing the mixture, causing the cells to produce the protein comprising etanercept; and (c) periodically or continuously removing spent culture medium from, and adding fresh culture medium to, the reaction vessel; wherein:

(i) dexamethasone, galactose and ManNAc are present in the culture medium in amounts sufficient to achieve said substantially matching glycosylation profile and (ii) the culture medium comprises feed media comprising the above-mentioned BalanCD/Hycell based medium mixture, CHOZN, glutamine and, optionally, cottonseed hydrolysate in amounts sufficient to achieve a production titer of correctly folded and incorrectly folded protein produced during the production phase of about 0.2 to about 1 g/L; and (iii) production of the protein comprising etanercept is carried out at a temperature selected from (i) greater than about 32° C.; (ii) greater than about 33° C.; (iii) greater than about 34° C.; (iv) greater than about 35° C.; (v) the range of about 33° C. to about 36° C.; (vi) the range of about 35° C. to about 36° C.; (vii) 32.5° C.; (viii) 33.5° C.; (ix) 34.5° C.; and (x) 35.5° C.

In yet a further embodiment, the disclosed method is a perfusion method for manufacturing etanercept comprising the following steps: (a) preparing a mixture comprising cells capable of expressing a protein comprising etanercept and a culture medium suitable for conducting such expression; (b) in a suitable vessel containing the mixture, causing the cells to produce the protein comprising etanercept; and (c) periodically or continuously removing spent culture medium from, and adding fresh culture medium to, the reaction vessel; wherein (i) step (b) is carried out at or above 33° C.; (ii) the culture medium comprises at least one of dexamethasone, galactose and ManNAc; (iii) the protein comprising etanercept comprises at least 60 wt. % correctly folded etanercept; (iv) the protein comprising etanercept is produced in titers of 0.2 to about 1 g/L; and (v) the etanercept has a glycosylation profile substantially similar to that of commercially available etanercept sold under the tradename Enbrel®. Preferably all three of the supplements galactose, dexamethasone and ManNAc are present in the culture medium. A particularly preferred production temperature is in the range of 33° C. to 34° C.

The present invention can produce correctly folded etanercept in excellent yields, having desired glycosylation profile necessary for therapeutic effect, and preferably at production temperatures higher than those previously thought necessary or desirable in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 9 through 13 depict the results of Hydrophobic Interaction Chromatography (HIC) of selected samples from media exchange study with respect to etanercept produced according to examples 1 and 2. Samples were subjected to HIC analysis after media exchange or harvest. Clipped, correctly folded, and misfolded product is indicated for each chromatogram. Integrations of the correctly folded peak are represented by the bar chart in FIG. 8.

FIG. 10 contains HIC chromatograms in which trace A is SF2, medium exchange 3 from FIG. 8; and trace B is SF3, medium exchange 1 from FIG. 8.

FIG. 11 contains HIC chromatograms in which trace A is SF3, medium exchange 3 from FIG. 8; and trace B is SF3, harvest from FIG. 8.

FIG. 12 contains HIC chromatograms in which trace A is SF4, media exchange 3 from FIG. 8; and trace B is SF5, media exchange 3 from FIG. 8.

FIG. 13 contains HIC chromatograms in which trace A is SF6, media exchange 3 from FIG. 8; and trace B is control shake flask, sampled at the media exchange 3 time point as represented in FIG. 8.

DETAILED DESCRIPTION OF THE INVENTION

Definitions

Figure 1:
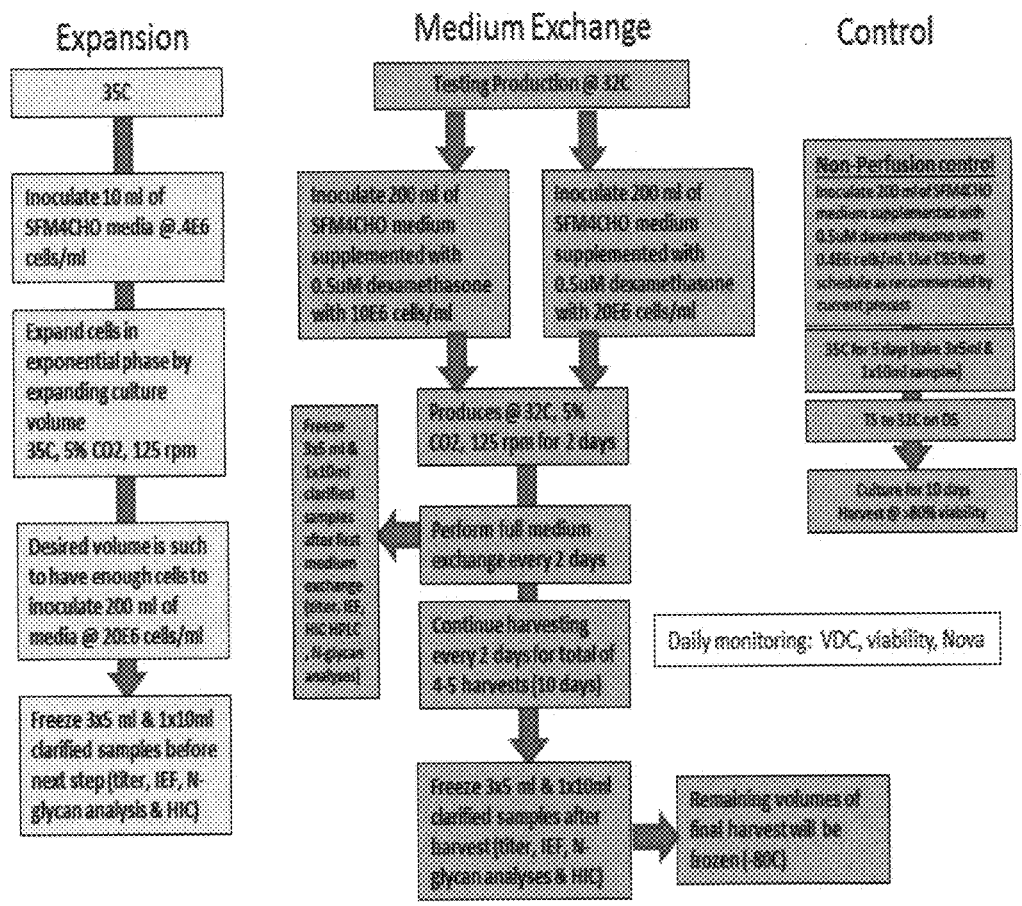
FIG. 1 shows a process of the present invention.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to the various embodiments given in this specification.

Unless otherwise defined, all technical and scientific terms used herein have the same meaning as commonly understood by one of ordinary skill in the art to which this invention pertains. In the case of conflict, the present document, including definitions will control.

The term "etanercept" as used herein refers to a polypeptide which is a dimeric fusion polypeptide consisting of the extracellular ligand-binding portion of the human 75 kilodalton (p75) tumor necrosis factor receptor (TNFR) linked to the Fc portion of human IgG1. It consists of 934 amino acids and has an apparent molecular weight of approximately 150 kilodaltons. For the purposes of the present application, the term "etanercept" also encompasses etanercept with minor modifications in the amino acid structure (including deletions, additions, and/or substitutions of amino acids) which do not significantly affect the function, potency, or avidity of etanercept. The term "etanercept" encompasses all forms and formulations of Enbrel®, including but not limited to concentrated formulations, injectable ready-to-use formulations; formulations reconstituted with water, alcohol, and/or other ingredients, and others. The term etanercept is also intended to include biosimilar or biobetter variants of the etanercept used in commercial Enbrel®. For example, a biosimilar or biobetter of etanercept may have a slightly different glycosylation profile than commercial Enbrel®. In addition a biosimilar or biobetter variant of the etanercept preparation found in commercial Enbrel® may exhibit a reduction in the amount of aggregates/misfolds present along with the active, properly folded etanercept ingredient.

The term "correctly folded etanercept" as used herein is intended to denote a folding conformation of the etanercept homodimer (as defined above) having biological activity for inhibition of TNF and conformation that are the same or substantially the same as the conformation and biological activity of the active ingredient in Enbrel®.

The term "incorrectly folded etanercept" as used herein is intended to encompass: (i) a homodimeric protein having the same amino acid sequence as etanercept (as defined above), but having a conformation different from that of correctly folded etanercept, wherein said different conformation renders the protein lacking or substantially lacking in biological activity as a TNF inhibitor; and/or (ii) an aggregate in which two or more correctly and/or incorrectly folded etanercept homodimers have become associated (i.e., aggregated or clumped) in such a manner as to form species having higher molecular weight than correctly folded etanercept; and/or (iii) a mixture of (i) and (ii); and/or (iv) aggregated i.e., clumped protein compositions comprising the same or essentially the same sequence, or portions thereof, as correctly folded etanercept but which exhibit decreased elution position (due to greater hydrophobicity) on an HIC column as compared to correctly folded etanercept.

The term "growth phase" denotes a phase in which cells capable of expressing etanercept are generally first cultured at a temperature which promotes exponential logarithmic growth of the cells prior to entering into the production phase. A suitable temperature for the growth phase is generally in the range of 34° C. to about 38° C. as described in U.S. Pat. No. 7,294,481.

The term "production phase is understood to have the same meaning as that ascribed in U.S. Pat. No. 7,294,481, incorporated by reference herein in its entirety. In particular, the term refers to the period during which cell growth has plateaued, i.e., logarithmic cell grown has ended, and protein production is primary. According to the present invention, the production phase is carried out under perfusion conditions, preferably at a temperature in the range of about 32.5° C. to about 37° C., and preferably in the range of about 33.5° C. to about 35.5° C.

Perfusion has the meaning generally explained below and can also be briefly understood as a method of culture in which waste medium (spent medium) is removed from the culture and the displaced medium is replenished with fresh medium. This may preferably be done in a continuous manner, but may also be performed in a stepwise discontinuous manner in which spent medium is replaced with fresh medium at desired intervals prior to completion of the production phase. The addition of fresh medium and elimination of waste products provides the cells with an environment that is better suited to achieving and maintaining high cell concentrations with higher productivity.

The term "treatment" refers to any administration or application of remedies for disease in a mammal and includes inhibiting the disease, arresting its development, relieving the disease (for example, by causing regression, or restoring or repairing a lost, missing, or defective function) or stimulating an inefficient process. The term includes obtaining a desired pharmacologic and/or physiologic effect and covering any treatment of a pathological condition or disorder in a mammal. The effect may be prophylactic in terms of completely or partially preventing a disorder or symptom thereof and/or may be therapeutic in terms of a partial or complete cure for a disorder and/or adverse effect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "composition" or "formulation" refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses or powders.

The terms "BalanCD/Hycell" denotes a mixture (approx. 1:1) of the commercially obtainable feeds sold as BalanCD™ CHO Growth A and HyClone™ Hycell CHO as referenced in the Table, below.

The following Table is a listing of the commercially available feeds and feed supplements useful in the present invention.

| Raw Material Description | Source | Vendor Catalog Number | Category | Stock Conc (g/L) | Useful Range | Use Notes |
|---|---|---|---|---|---|---|
| BalanCD ™ CHO Growth A | Irvine Scientific | 94120-10L | Base medium | 23.725 | n.a. | base medium |
| HyClone ™ HyCell CHO | Thermo Scientific | SH30933 | Base medium | 25.400 | n.a. | base medium |
| HyClone ™ SFM4CHO | Thermo Scientific | SH30518.04 | Base medium | 19.830 | n.a. | used in seed train; |
| D-(+)-Galactose | SAFC | G5388 | Glycan feed | | ≤10 mM | used at 10 mM final; to optimize product quality |
| Dexamethasone | SAFC | D4902 | Glycan feed | | ≤1 uM | used at 0.8-1.0 uM; to optimize product quality |
| ManNAc (N-acetylmannosamine) | SAFC | A8176 | Glycan feed | | ≤20 mM | used at 10-20 mM final; to optimize product quality |
| BalanCD ™ CHO Feed 1 | Irvine Scientific | 94119-10L | Titer feed | 55.776 | 10% (v/v) | Boosts titer when added alone or with CHOZN |
| BalanCD(tm) CHO Feed 2 | Irvine Scientific | 94121 | Titer feed | | | |
| HyClone ™ Cell Boost 5 | Thermo Scientific | SH30865.04 | Titer feed | 50 | 10-20% (v/v) | Used in control experiments |
| CHO CD EfficientFeed A | Life Technologies | A1023401 | Titer feeds | | | Boosts titer when added alone or with with CHOZN |
| Cottonseed Hydrolysate ("CSH") | FrieslandCampina Domo | CNE50M-UF | Titer feed | 100 | 15% (v/v) | increases cell growth and specific productivity |
| EX-Cell CHOZN Platform Feed | SAFC | 24331C-10L | Titer feed | 50 | 10-20% (v/v) | complex feed; boosts titer when added alone or in combination with other complex feeds |

Perfusion-Based Manufacture of Etanercept

The present invention provides methods of manufacturing etanercept which involve the use of perfusion. The term "perfusion" as used herein is intended to generally denote a process in which a suspension cell culture is continuously or periodically, and most preferably continuously, supplied with fresh medium to a bioreactor while spent culture media is continuously removed, i.e., harvested (preferably with the product) in order that product contained therein can be continuously harvested, and the waste and toxic materials present in the spent medium can be removed from the bioreactor. Using appropriate filtration means well known in the art, the cells are then continuously filtered from the harvest stream and returned to the bioreactor to maintain a constant culture volume. Such a process, typically carried out continuously, allows the cells to reach high densities. Accordingly, densities as high as 15-20 million cells/mL can routinely be reached and maintained for extended periods of time, e.g. at least two weeks. This can result in very highly productive cell culture process that can produce for a longer period of time as opposed to batch or fed-batch cultures. Alternatively, rather than continuously harvesting product from the removed spent medium, the product can be maintained and concentrated in the culture, and then harvested periodically, or at the end of the culture. Utilization of appropriate size filters can allow for removal of only waste, with retention of the recombinant product in the bioreactor culture. In such a process, sometimes referred to as "extreme density" or XD process, the product can be harvested periodically or at the end of the culture.

We have now found that a predetermined glycoprofile of etanercept produced in a perfusion process can be achieved when the culture medium comprises at least one of dexamethasone, galactose and ManNAc, and most preferably when all three are present in the culture medium. Suitable amounts are referenced in the Examples below. We have also discovered that the additional presence of cottonseed hydroysates in such perfusion process can further enhance the glycoprofile. The term "glycoprofile" or "glycosylation profile" are well understood in the art, and should be understood to include the level or degree of sialylation occurring on the glycan groups attached to the etanercept protein.

Example 1

A shake flask format is used to investigate processing conditions similar and comparable to a perfusion process. High density shake flask cultures (5 million cells per milliliter to 20 million cells per milliliter) are established from cultures expanded at temperatures in the range of about 35° C. to 37° C. in SFM4CHO medium supplemented with Cell Boost 5 feed and about 0.5 uM-1 uM dexamethasone.

Example 1 Media Formulation

| Feed Component | Concentration |
| --- | --- |
| SFM4CHO | 1x |
| Cell Boost 5 | 20% |
| Dexamethasone | 0.5 uM |

Each culture, maintained in temperatures ranging from 32° C. to 35.5° C., was allowed to produce Etanercept protein for two days before medium was fully exchanged for a subsequent round of production. These 2-day harvest intervals are comparable to a perfusion rate of 0.5 bioreactor volume per day. The medium exchange is repeated 4 times (4 cycles). Harvested media is frozen at −80° C. Titers are analyzed by ForteBio and TNF-binding ELISA. Additionally each sample is assessed for N-linked glycoprofile, protein charge distribution by IEF gel and for protein folding by hydrophobic interaction chromatography (HIC).

Figure 2:
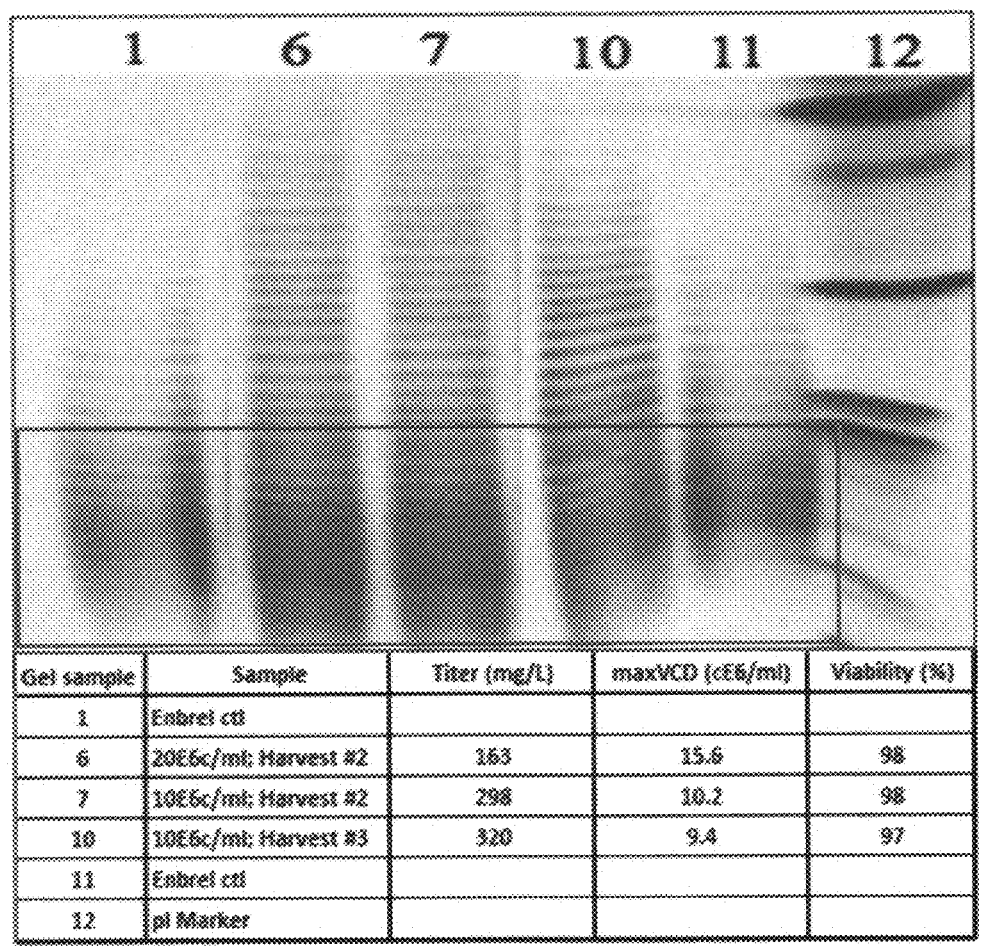
FIG. 2 shows IEF gels with charge profiles for etanercept samples produced using the process of the invention.
Figure 3:
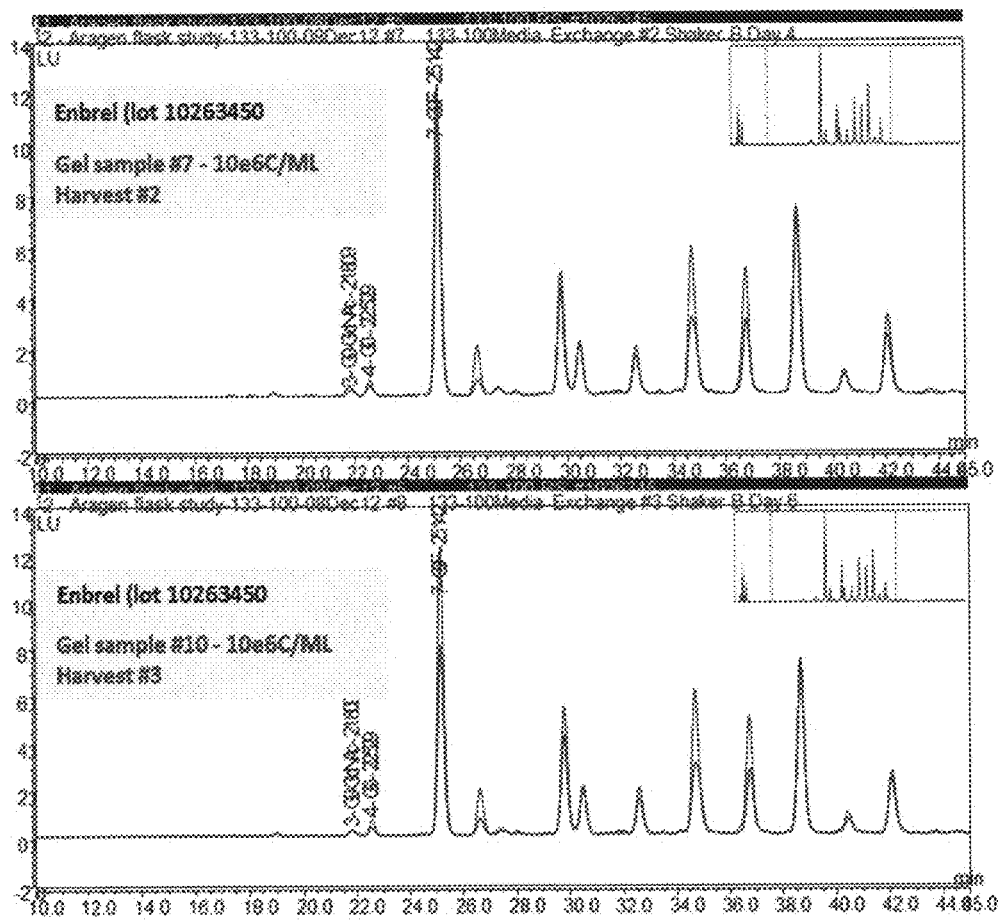
FIG. 3 shows N-glycan analysis of etanercept samples produced using the process of the invention.

In order to support the high cell numbers necessary for inoculation of high density production cultures typically achieved in a perfusion process, the seed train is conducted in large volume shake flasks maintained at 35° C. or 37° C., 5% CO2 level and the speed of the orbital shaker is adjusted to 125 rpm. Production phase shake flasks containing SFM4CHO medium supplemented with Cell Boost 5 feed and 0.5 uM dexamethasone are inoculated at cell densities either 10 million cells per milliliter or 20 million cells per milliliter. The production phase is conducted at a temperature in the range of about 32° C. to about 36° C., otherwise all other culture conditions are the same. Cultures are monitored daily for viable cells densities and viabilities. To investigate reactor volume exchange conditions comparable to a perfusion rate of 0.5 bioreactor volume per day, the medium in each culture was fully exchanged every 48 hours. The harvested and clarified media are frozen at −80° C. Following each spent medium harvest, cells are resuspended in fresh medium and allowed to accumulate recombinant product for another 48 hours, the aforementioned process being repeated for a total of 4 cycles. At the conclusion of the experiment all samples are thawed and analyzed with respect to charge profile (by isoelectrofocusing gels, IEF), N-glycan profile and titers. A control experiment was conducted using a fed-batch culture inoculated at 0.4 million cells per milliliter in SFM4CHO medium supplemented with Cell Boost 5 feed and 0.5 uM dexamethasone. The conditions for the control experiment involved an expansion phase at 35° C. and the production phase at 32° C. initiated on day 5. The Etanercept protein produced in the control experiment is allowed to accumulate without medium exchange for the length of the experiment. Samples from the control culture are withdrawn every 48 hours during the production phase, frozen at −80° C., and analyzed along with the remaining experimental samples. The experimental design of the experiments conducted according to this Example 1 is depicted in FIG. 1. The charge profile of etanercept produced in this Example is shown in FIG. 2. FIG. 3 shows the N-Glycan analysis of Gel #7 and Gel #10 of FIG. 2. Etanercept protein produced in this example using a medium exchange technique designed to simulate perfusion processing elicits a similar profile to that of the innovator based on charge profile assessed by IEF gel and titers (FIG. 2). The N-glycan distribution shown by chromatograms in FIG. 3 has also similar profile to the reference standard. Based on the productivities determined to be approximately 0.3 g/L from culture at cell density of 10 million cells per milliliter, we expect the disclosed method to achieve production of approximately 0.75 to 1 g/L per day based on culture at expected minimum density of 50 million cells per milliliter.

Example 2

In order to support the high cell numbers necessary for inoculation of high density production cultures characteristic of perfusion processes, the seed train is conducted in large volume shake flasks maintained at 35° C. or 37° C., 5% CO2 level and the speed of the orbital shaker is adjusted to 125 rpm. Production phase shake flasks containing SFM4CHO medium supplemented with Cell Boost 5 feed and 0.5 uM dexamethasone are inoculated at cell densities either 5 million cells per milliliter or 8 million cells per milliliter. The following media formulation was used.

Example 2 Media Formulation

| Feed Component | Concentration |
| --- | --- |
| SFM4CHO | 1x |
| Cell Boost 5 | 20% |
| Dexamethasone | 0.5 uM |

Figure 4:
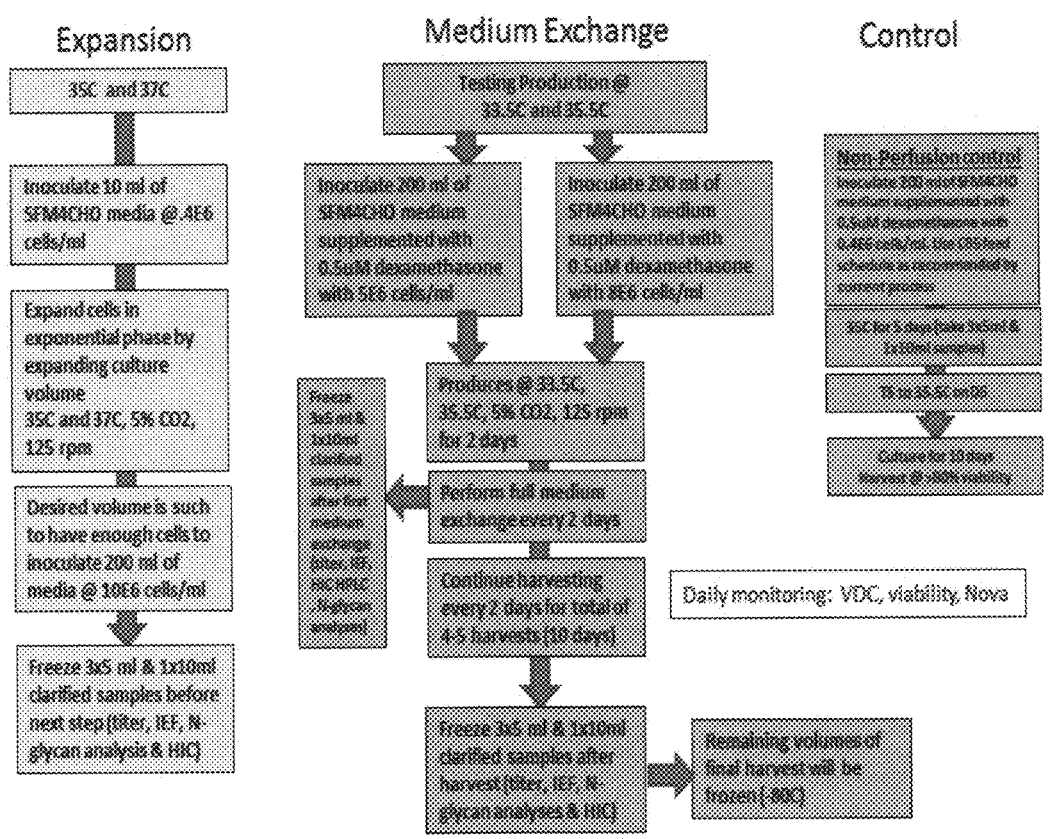
FIG. 4 shows a process of the present invention.
Figure 5:
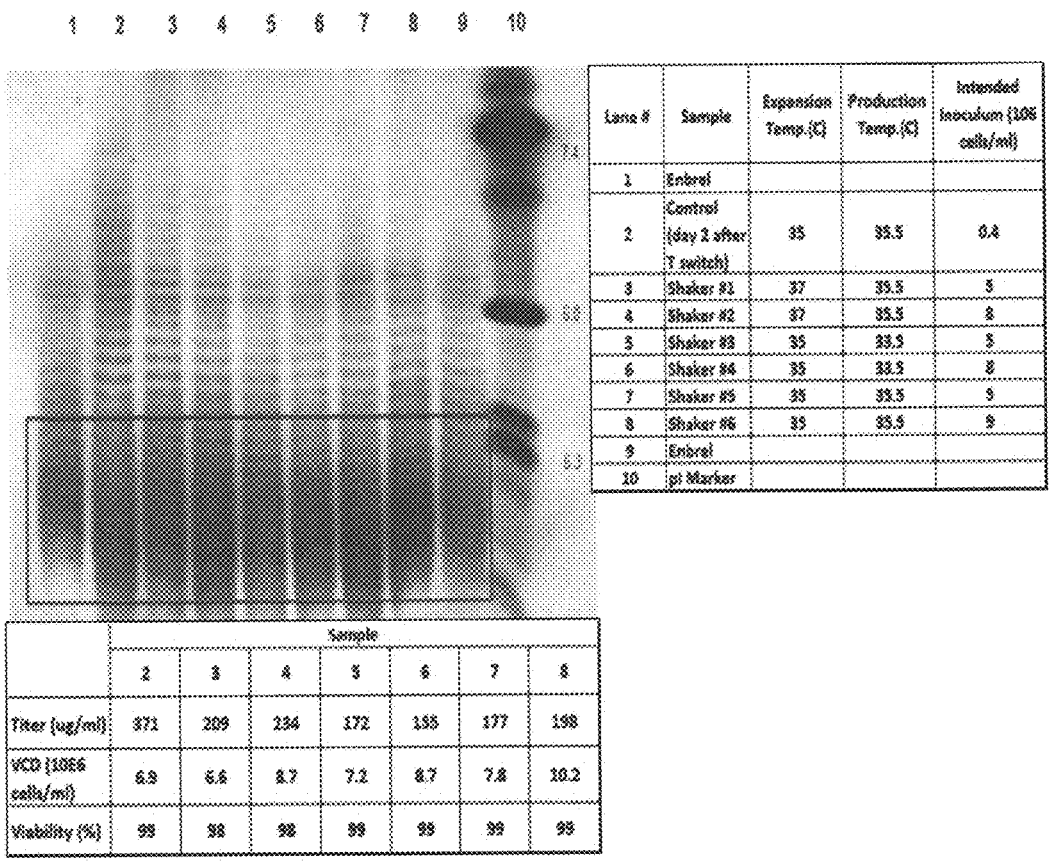
FIG. 5 shows IEF gels with charge profiles for etanercept samples produced using the process of the invention.
Figure 6:
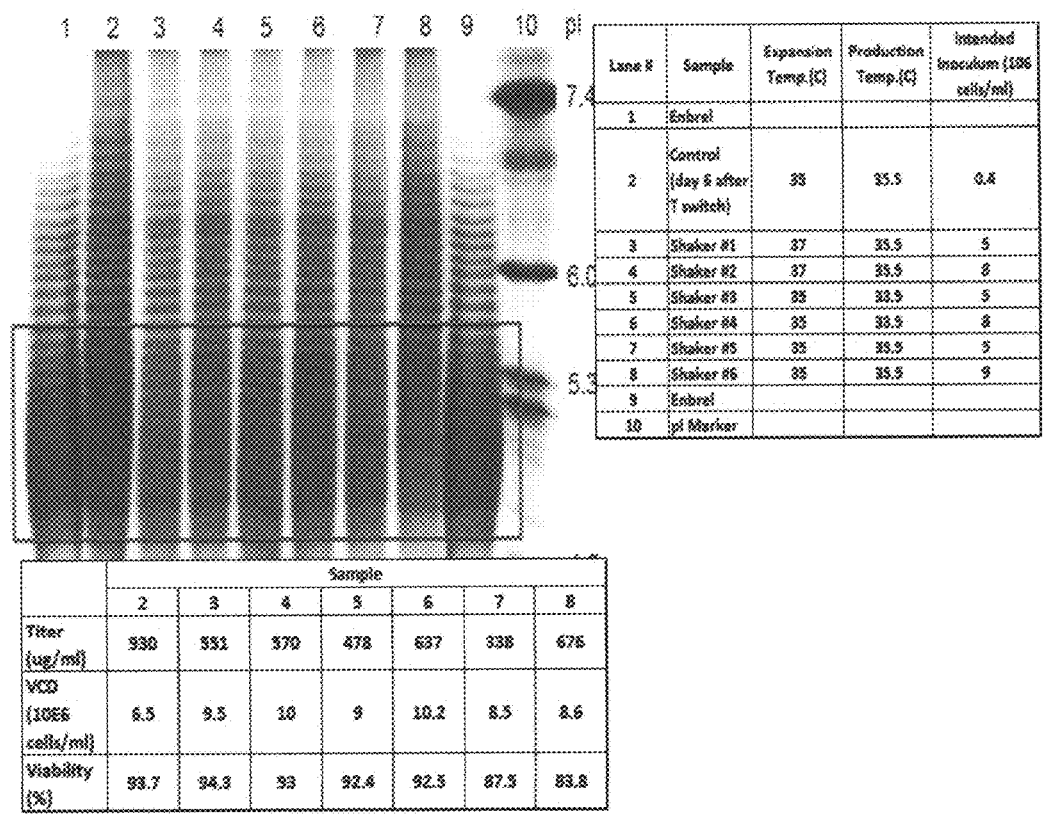
FIG. 6 shows IEF gels with charge profiles for etanercept samples produced using the process of the invention.
Figure 7:
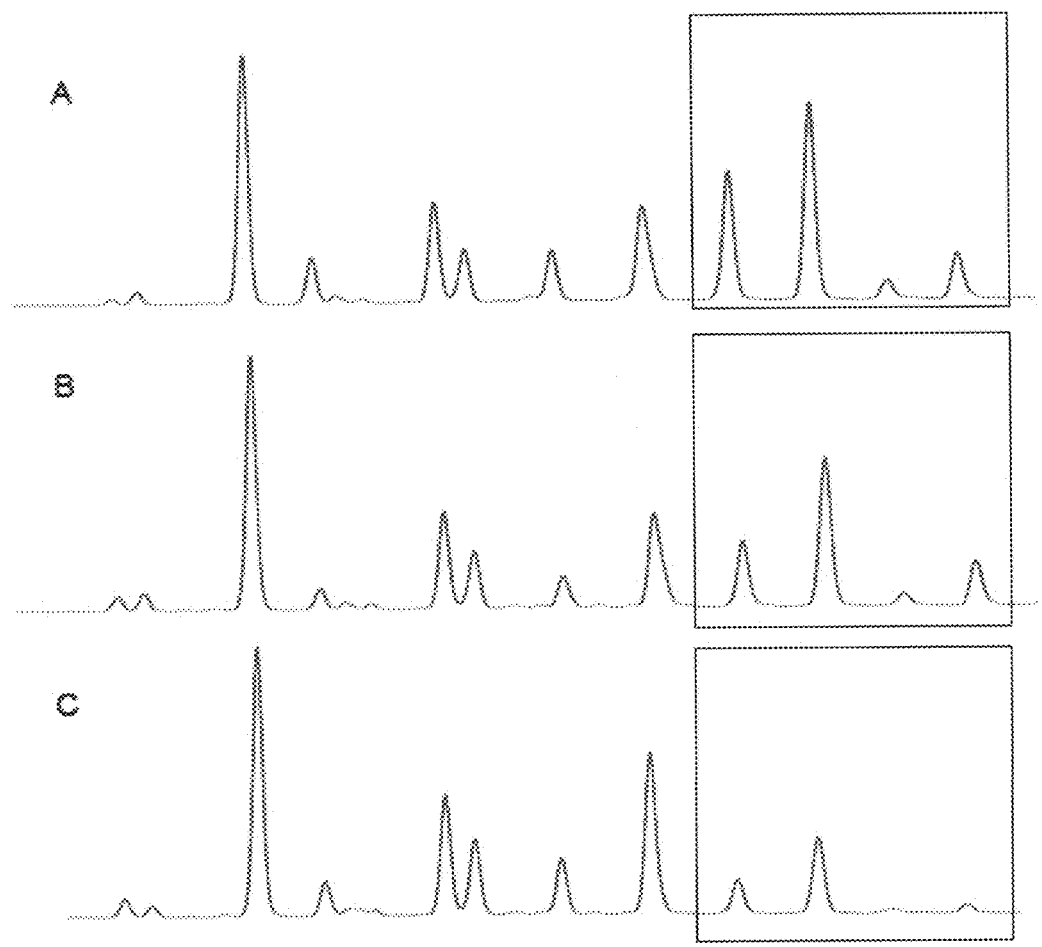
FIG. 7 shows N-Glycan analysis of etanercept samples produced using the process of the invention. Chromatograms are of innovator protein (panel A), the third medium exchange of Shake Flask 3 (panel B), and appropriate harvest from the fed-batch Control Flask (panel C).
Figure 8:
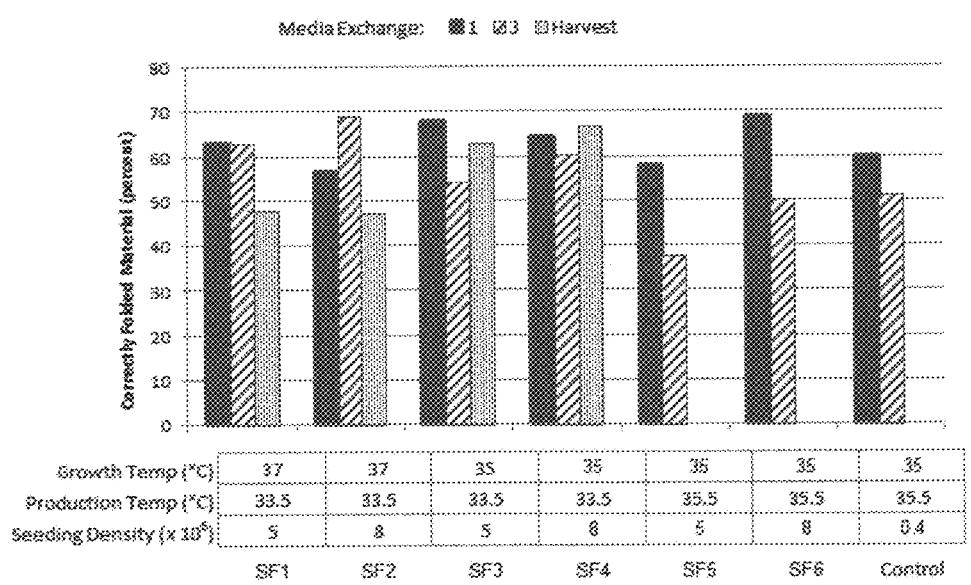
FIG. 8 is a bar graph representing the percent of correctly folded etanercept produced in the working examples, as determined by HIC chromatography (including Enbrel control). Cultures were expanded under the conditions indicated (growth temperature), and product was produced (production temperature) in shake flasks seeded at the indicated concentrations. Bars indicated percent of material in the peak representing correctly folded product from chromatograms such as those shown in FIGS. 9 through 13.
Figure 9:
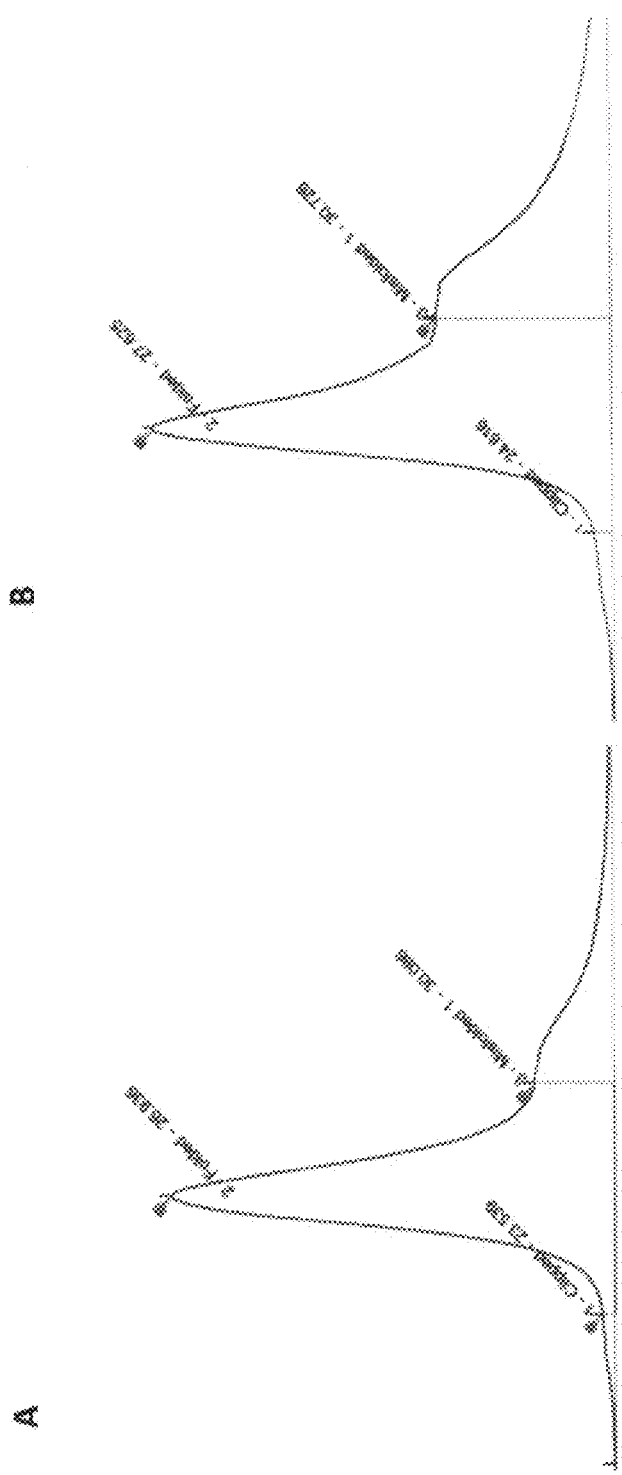
FIG. 9 contains HIC chromatograms in which trace A is Enbrel control and trace B is SF1, medium exchange 3 from FIG. 8.
Figure 10:
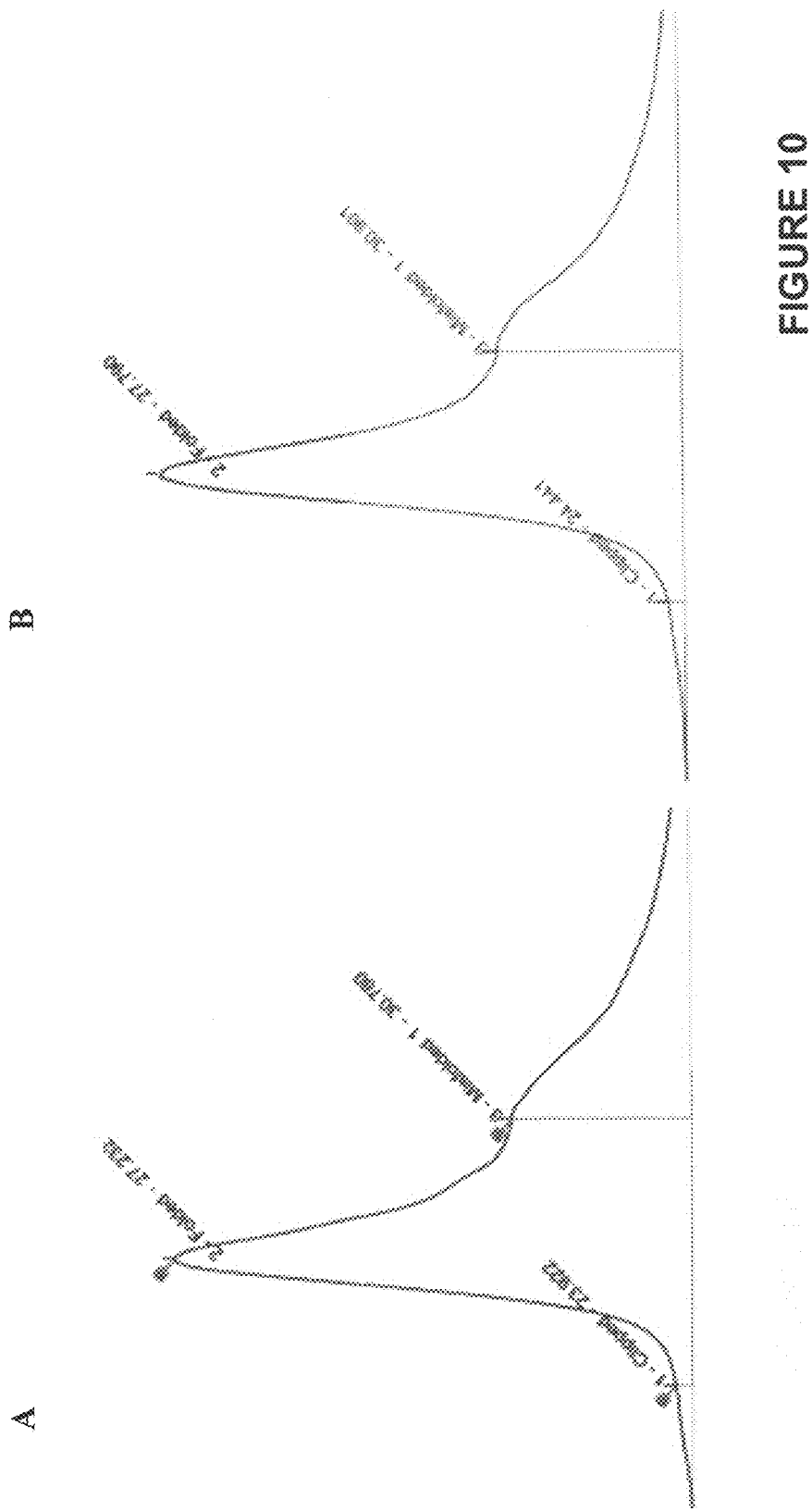
Figure 11:
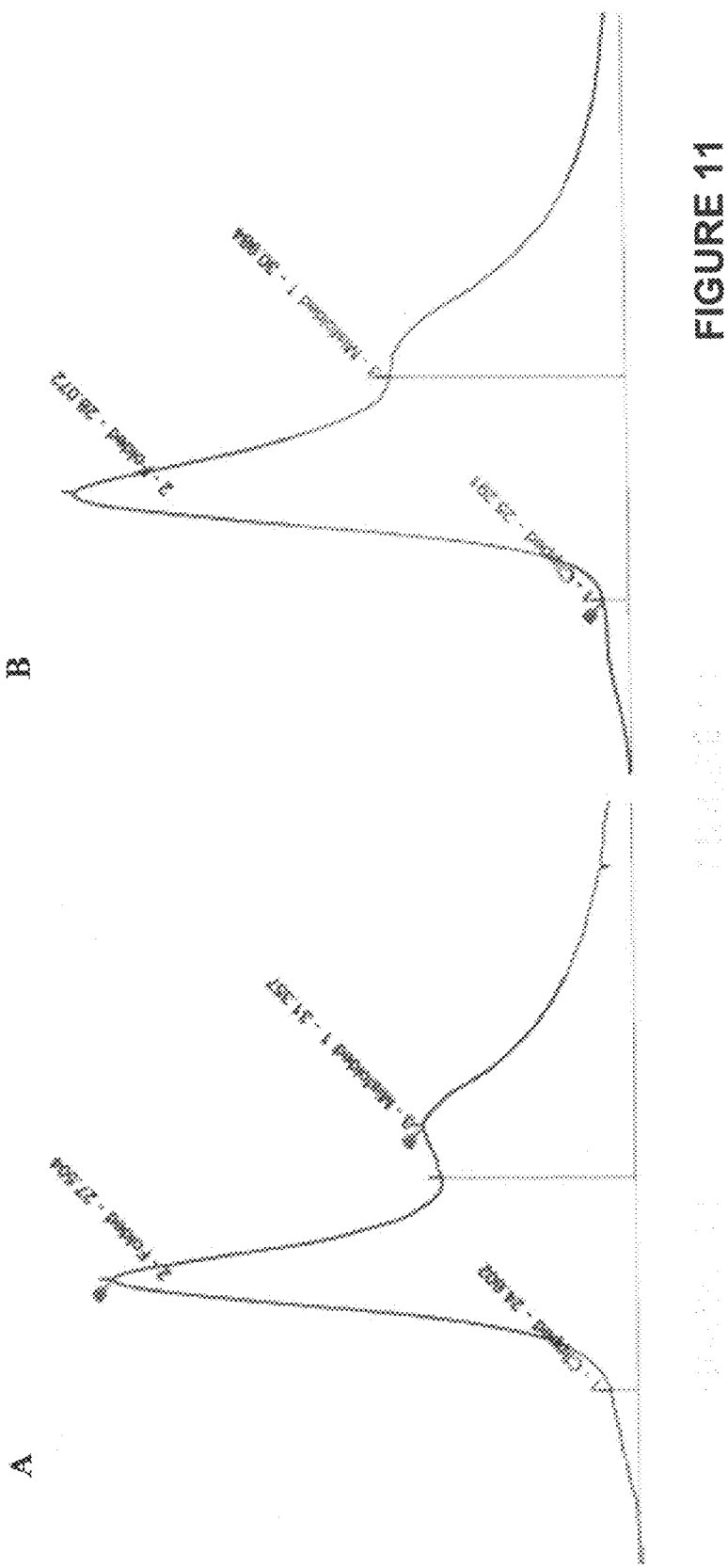
Figure 12:
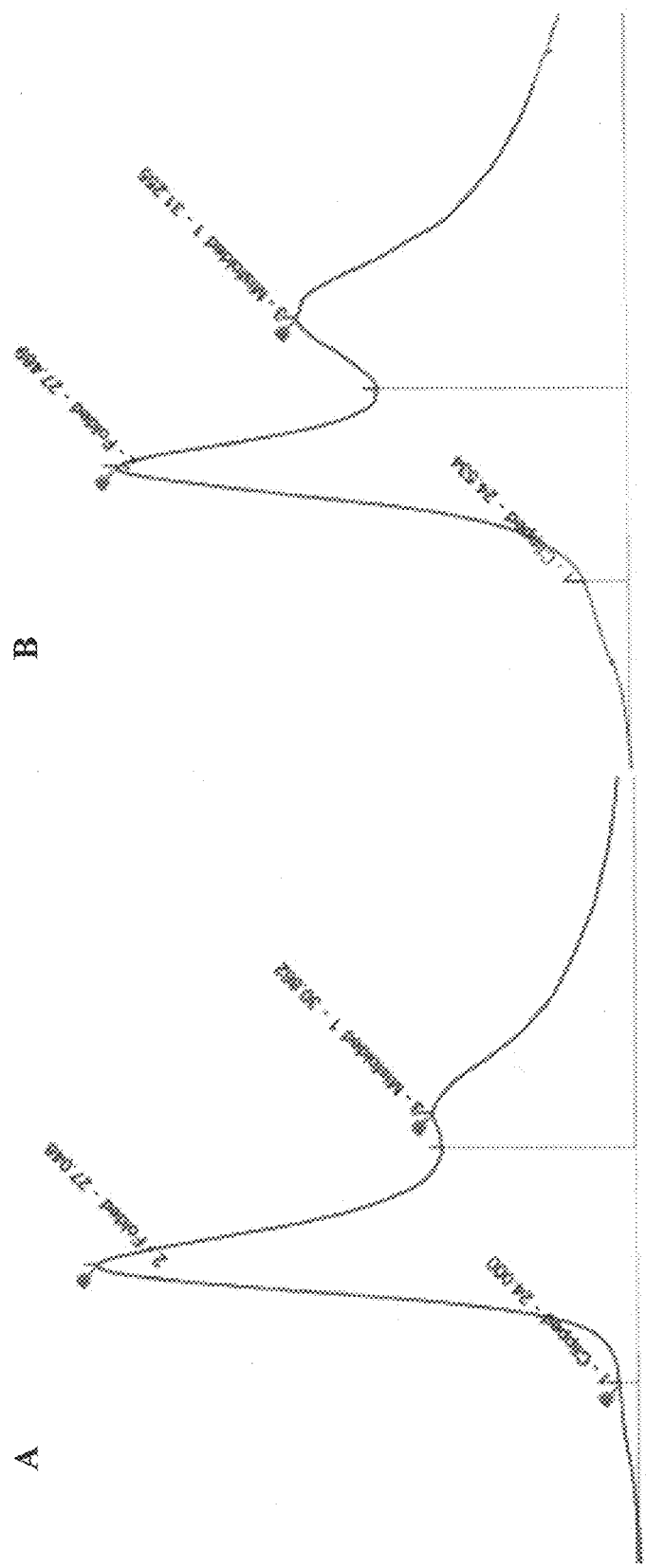

The production phase is conducted at temperatures 33.5° C. or 35.5° C., otherwise all other culture conditions are the same. Cultures are monitored daily for viable cells densities and viabilities. To achieve the equivalent of a perfusion rate of 0.5 bioreactor volume per day the medium in each culture is fully exchanged every 48 hours. The harvested, clarified spent media is frozen at −80° C. Following each spent medium harvest, cells were resuspended in fresh medium and allowed to accumulate recombinant product for another 48 hours; with the aforementioned process being repeated for a total of 5 cycles. At the conclusion of the experiment, all samples were thawed and analyzed with respect to titers, charge profile (by isoelectrofocusing gels, IEF), N-glycan profile and folding. Control conditions involved fed-batch culture inoculated at 0.4 million cells per milliliter in SFM4CHO medium supplemented with Cell Boost 5 feed and 0.5 uM dexamethasone. The control conditions involved the expansion phase conducted at 35° C. and the production phase at 35.5° C. initiated on day 5. The Etanercept protein was allowed to accumulate without medium exchange for the length of the experiment. Samples from the control culture were withdrawn every 48 hours during the production phase, frozen at −80° C., and analyzed along with the remaining experimental samples. The experimental design of the experiments conducted according to this Example 2 is depicted in FIG. 4. FIG. 5 shows the IEF gels for etanercept harvested after medium exchange #1 (i.e., 2 days after initiation of production phase). IEF gels in FIG. 5 show charge profile of Etanercept proteins produced after first medium exchange (equivalent of day 2 of a continuous perfusion) similar to that of Enbrel®. The control sample which is at this point still at low cell density shows similar profile. FIG. 6 shows the IEF gels for etanercept harvested after medium exchange #3 (6 days after initiation of production phase). The charge profile of Etanercept proteins produced after third medium exchange (equivalent to day 6 of a continuous perfusion) is similar to that of Enbrel®. The desired isoforms are enclosed by a red box. Control sample shows some deterioration of product quality as shown by higher content of undersialylated, higher pI protein species. The data in this Example lends support to a conclusion that a perfusion system can provide a better protein quality than the fed-batch culture. Samples from each medium exchange are subjected to N-glycan analysis (Melmer et al., Anal Bioanal Chem (2010) 398:905-914, HILIC analysis of fluorescence-labeled N-glycans from recombinant biopharmaceuticals). Briefly, glycans are released from the test material, labeled with a fluorescent moiety to permit detection, and fractionated by normal-phase HPLC. Chromatograms of innovator protein (panel A), the third medium exchange of Shake Flask 3 (panel B), and appropriate harvest from the fed-batch Control Flask (panel C) are shown in FIG. 7.

Example 3

The seed train is expanded in large-volume shake flasks at 35° C. in SFM4CHO. The production bioreactor is inoculated at seeding densities of from 1 to 5×10$^6$ cells/mL in SFM4CHO containing Cell Boost 5 0.5 uM dexamethasone Table 1), and maintained at temperatures from 33.5° C. to 35° C. The media formulation was as follows:

Example 3 Media Formulation

| Feed Component | Concentration |
| --- | --- |
| SFM4CHO | 1x |
| Cell Boost 5 | 20% |
| Dexamethasone | 0.5 uM |

An ATF™ cell retention device (Refine Technology) is used to recirculate medium (containing waste products and desired product) past a hollow fiber filter, with recirculation rates from 0.1 to 2.0 working culture volumes per minute. The culture is expanded for 0 to 2 days, and then perfusion is initiated at rates from 0.2 to 2 culture volumes per day. New medium is added as spent medium, containing the product, is harvested through a 0.2 urn pore size hollow fiber filter. Harvested fluid is chilled to 2-8° C., purified by capture on protein A resin. Aliquots are analyzed for titer and N-glycan distribution, as described for Examples 1 and 2. HIC analysis may be used to evaluate the relative amounts of properly folded etanercept, versus improperly folded/aggregated (inactive) material.

Figure 14:
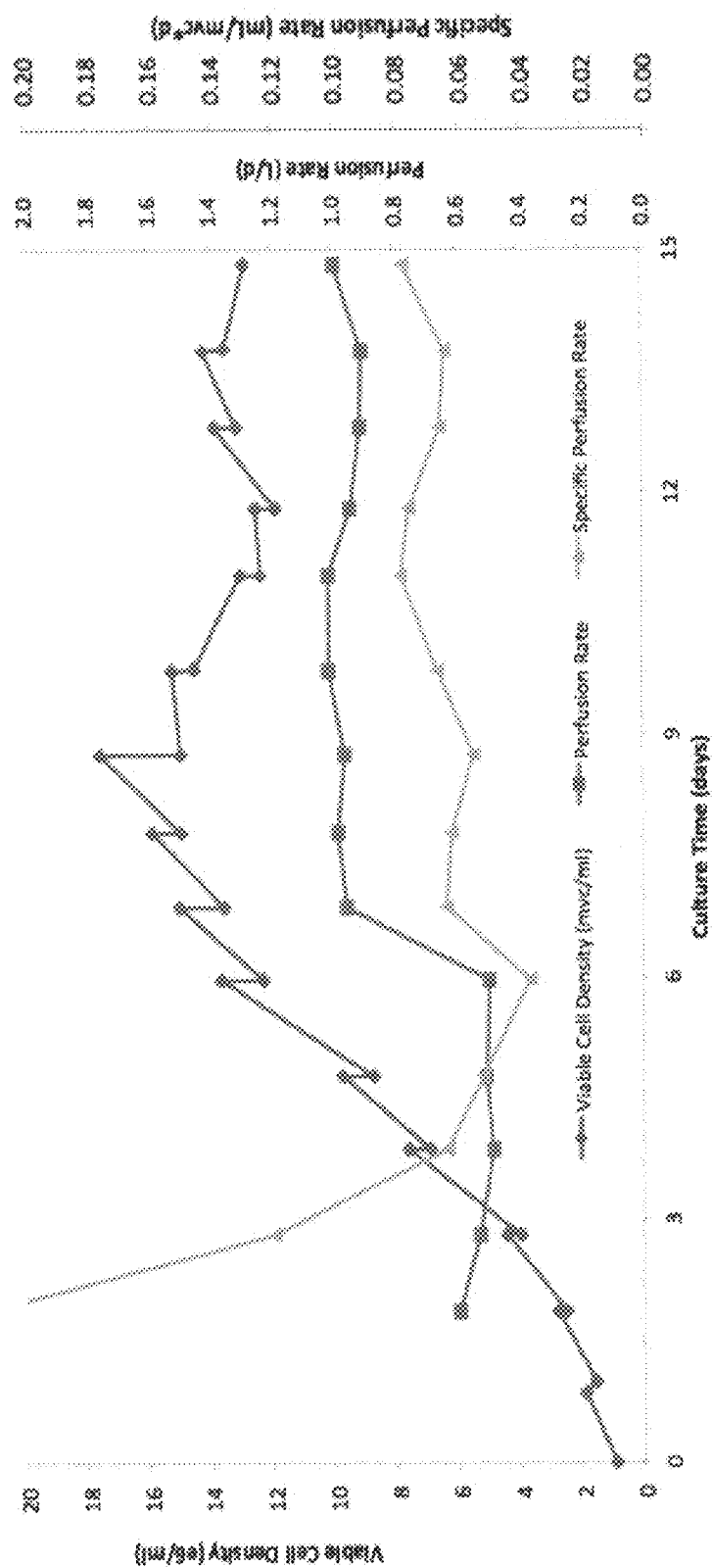
FIG. 14 contains the viable cell density, perfusion rate, and specific perfusion rate from the perfusion bioreactor of Example 3.
Figure 15:
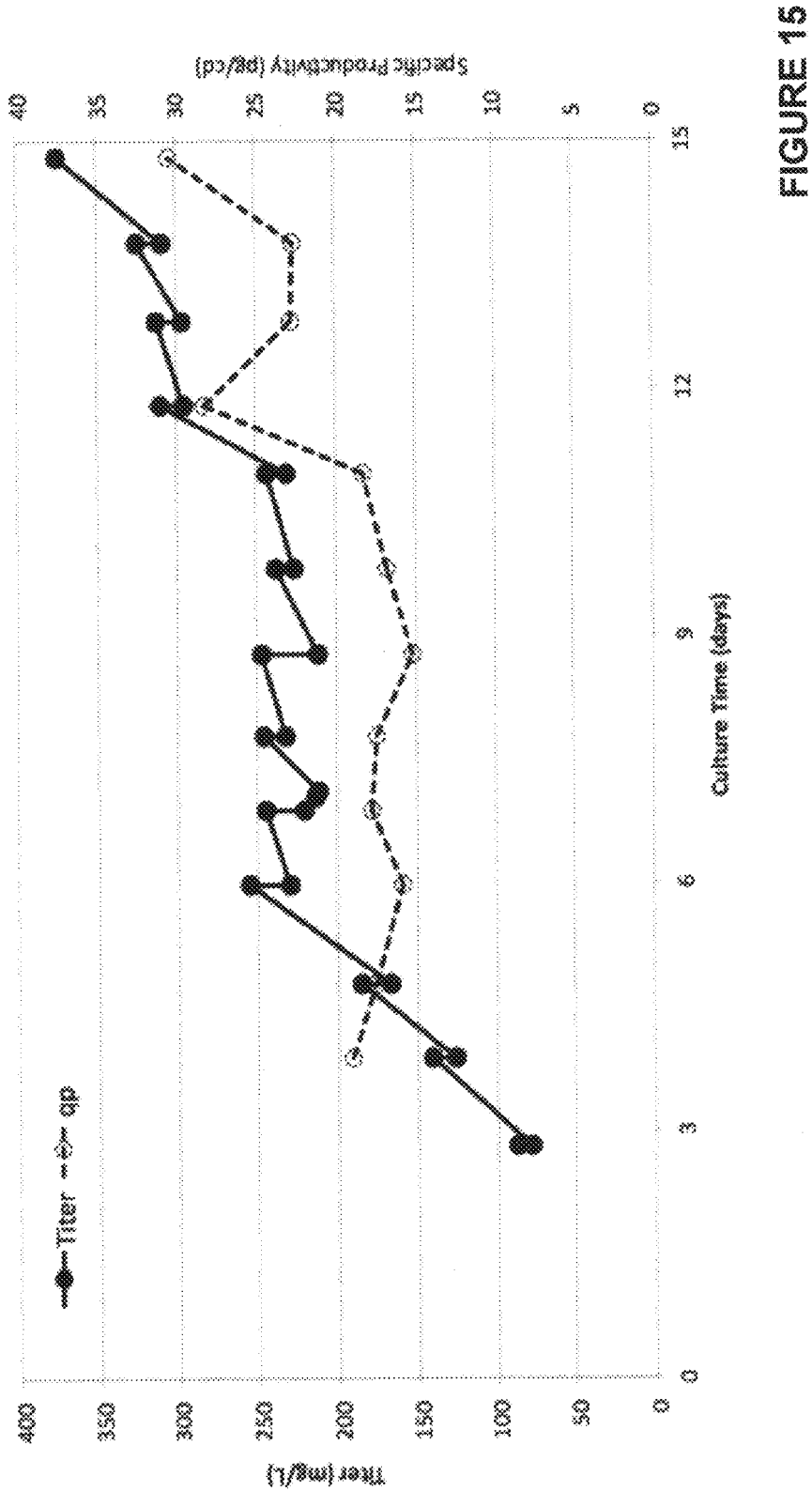
FIG. 15 contains the titer and specific productivity of the perfusion culture of Example 3.

FIG. 14 shows the VCD, which reached around 12×10$^6$ cells/mL during the perfusion production phase. The perfusion rate, which began at 0.5 volumes of medium added per bioreactor volume per day (WD) and increased to 1.0 VVD when the VCD reached its plateau. The specific perfusion rate (mL of media per million cells per day) ranged from 0.06 to 0.08 during the production phase. The titer in samples taken daily was 250 to 350 mg/L, while the specific productivity was 15 to 30 pg per cell per day (FIG. 15).

Figure 16:
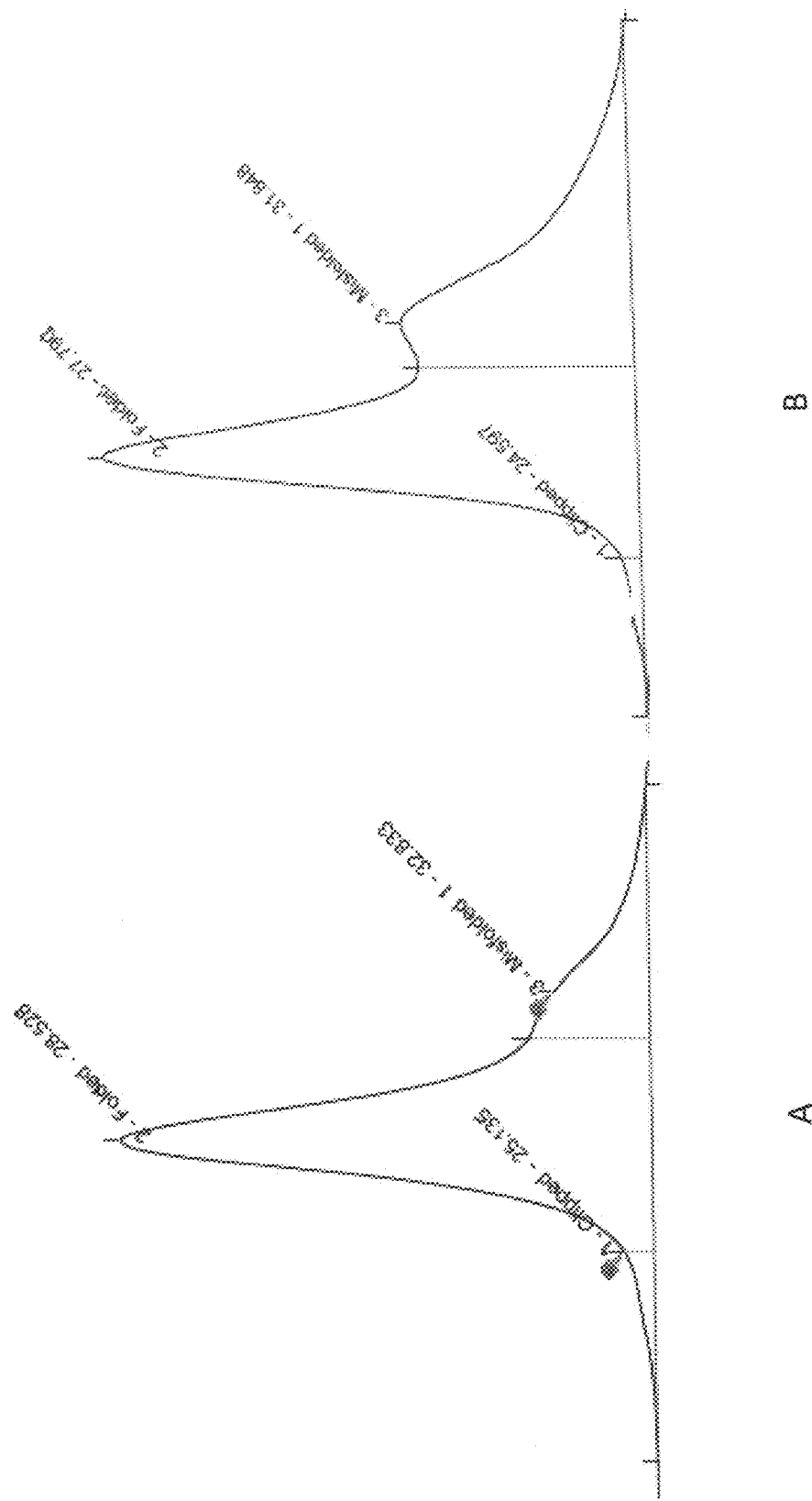
FIG. 16 contains HIC chromatograms in which trace A is Enbrel control, trace B is a sample from the harvest of a fed-batch bioreactor, trace C is from day 9 of the perfusion bioreactor in FIG. 14, and trace D is from day 12 of the perfusion bioreactor in FIG. 14.
Figure 16:
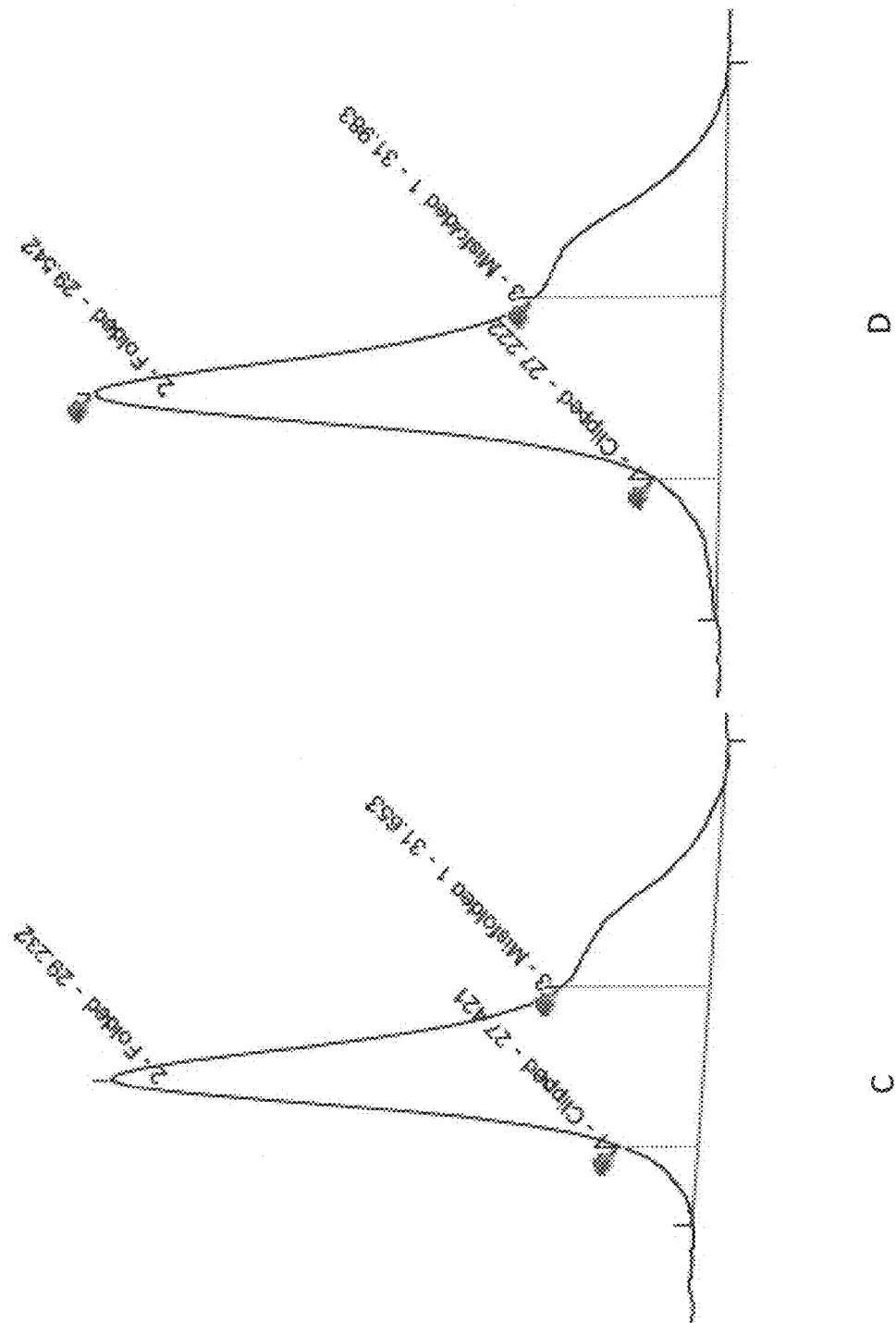

Analysis of correct folding, using HIC, shows that etanercept-containing material from the perfusion bioreactor has a higher percentage of correctly folded etanercept than that produced in a fed-batch culture (compare FIG. 16 panel B, fed-batch, to panels C and D, perfusion).

Figure 17:
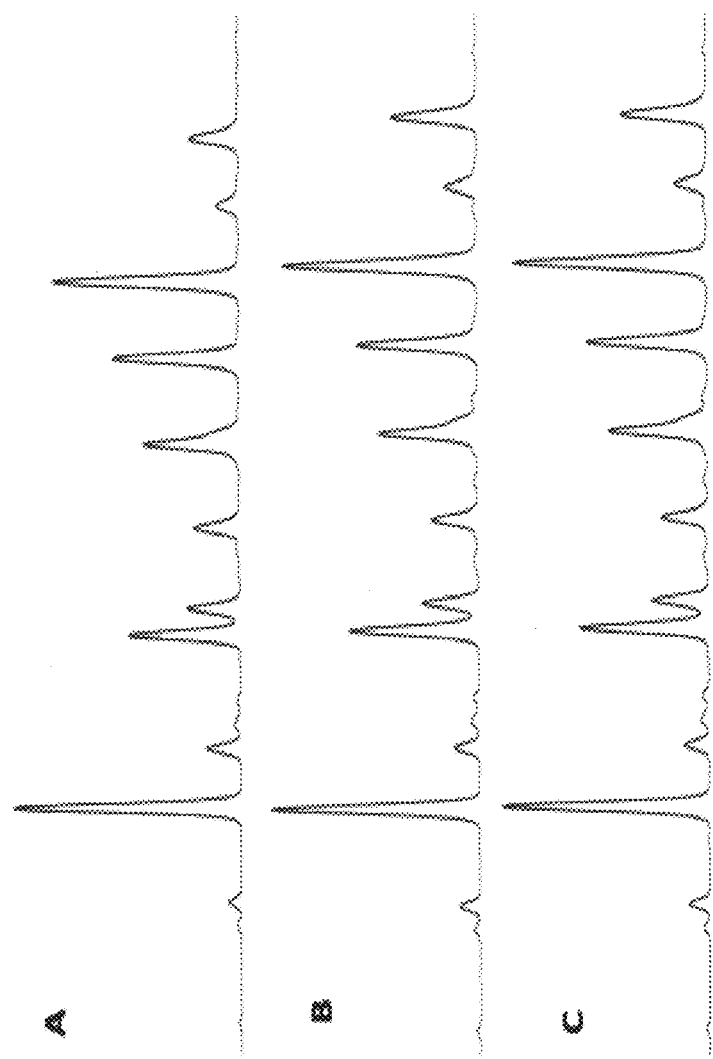
FIG. 17 contains the N-glycan chromatograms of Enbrel reference (A), a sample of CHS-0214 from day 9 of the perfusion bioreactor (B), and a sample of CHS-0214 from day 12 of the perfusion sample (C) shown in FIG. 14.

N-glycan analysis shows the close agreement between etanercept produced in a perfusion bioreactor and Enbrel® reference, as shown in the chromatograms in FIG. 17.

Example 4

Cells were inoculated at 25 million cells per milliliter of media into two different base media, SFM4CHO or BalanCD/Hycell, each supplemented with Cell Boost (in the case of SFM4CHO) or CHOZN feeds (in the case of BalanCD/Hycell) at final concentration of 10% or 20%. The feeds also included other supplements that can promote sialylation, i.e., dexamethasone, galactose and ManNAc. Cottonseed hydrolysates and galactose were also added to the BalanCD/Hycell-containing medium (see formulation summaries below)

Example 4 (SF1)

| Feed Component | Concentration |
| --- | --- |
| SFM4CHO | 1x |
| Cell Boost 5 | 10% |
| Dexamethasone | 0.8 uM |

Example 4 (SF2)

| Feed Component | Concentration |
| --- | --- |
| SFM4CHO | 1x |
| Cell Boost 5 | 20% |
| Dexamethasone | 0.8 uM |

Example 4 (SF3)

| Feed Component | Concentration |
| --- | --- |
| BalanCD/Hycell | 1:1 |
| CHOZN | 10% |
| Cotton Seed Hydrolysate | 7.5% |
| Galactose | 10 mM |
| ManNAc | 10 mM |

Example 4 (SF4)

| Feed Component | Concentration |
| --- | --- |
| BalanCD/Hycell | 1:1 |
| CHOZN | 20% |
| Cotton Seed Hydrolysate | 7.5% |
| Galactose | 10 mM |
| ManNAc | 10 mM |

Figures 18, 19:
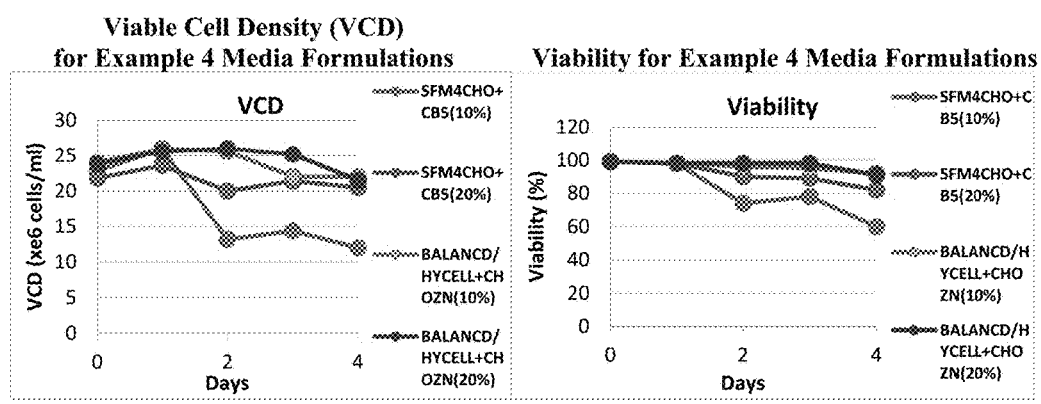
FIG. 18 is a chart of culture viable cell density (VCD) for media formulations of Example 4.
FIG. 19 is a chart of viability for media formulations of Example 4.
Figure 20:
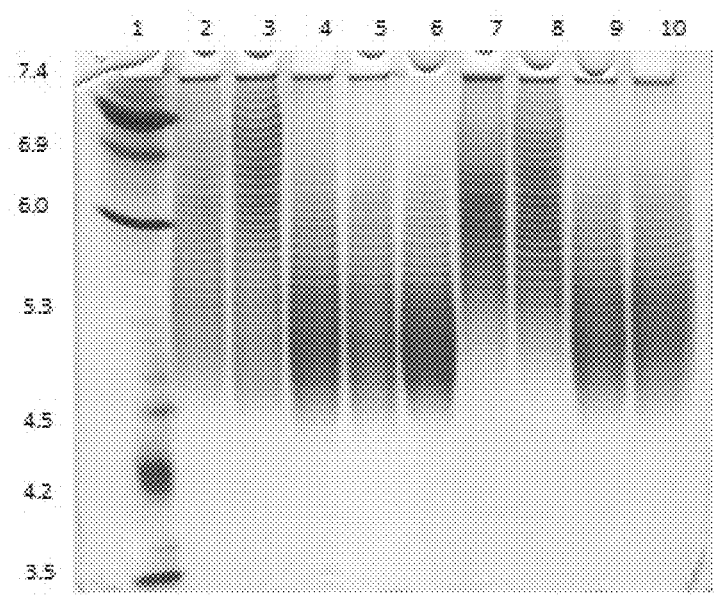
FIG. 20 is a photograph of isoelectrofocusing (IEF) Gel for media formulations of Example 4.

Cultures were maintained at a temperature of 33.5° C. while perfusion was carried out by exchanging media every 48 hours. Samples from each medium exchange were analyzed with respect to titers, isoform profile by IEF gels and for amino acid depletion profile (spent medium analysis). Culture viable cell density (VCD) and viability are shown in FIGS. 18 and 19, respectively, while isoform profile correlating with the level of a sialic acid content is shown in FIG. 20 (IEF Gel for Example 4). The titers were evaluated by ForteBio analysis and are displayed in FIG. 21 (Titer Graph for Example 4).

FIGS. 18 and 19 show viable cell density (VCD) and viability profile of cultures maintained in the four above referenced media formulations (SF1 to SF4). BalanCD/Hycell medium supplemented with CHOZN (10% or 20%) and cottonseed hydrolysate, galactose and ManNAc supports better nutrition resulting in superior viability, VCD, product quality (see FIG. 20) and titers (see FIG. 21).

FIG. 20 shows isoform profile of proteins isolated from cultures cultivated in SFM4CHO medium (lanes 2, 3, 7, 8) or in BalanCD/Hycell medium (lanes 4, 5, 9, 10). Proteins isolated from SFM4CHO cultures show reduced sialylation compared to reference standard (lane 6) while proteins isolated from BalanCD/Hycell cultures display isoform profile based on sialic acid content closely matching that of the reference standard.

Figure 21:
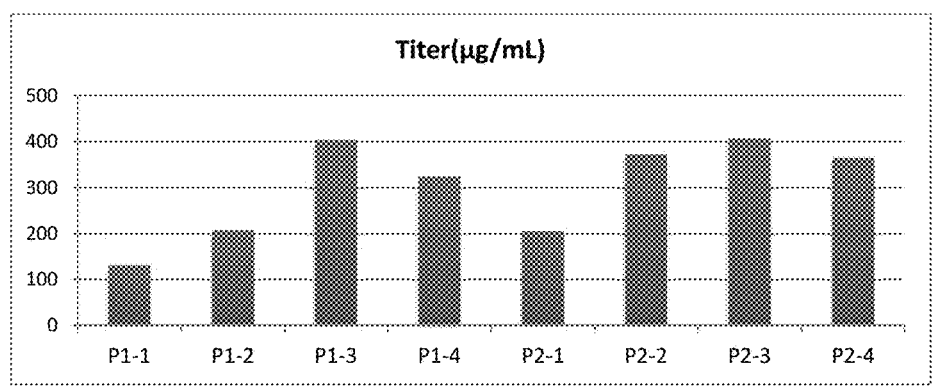
FIG. 21 is a titer graph for media formulations of Example 4.

FIG. 21 shows that cultures from SFM4CHO medium (P1-1, P1-2, P2-1, P2-2) displayed lower productivity than those cultivated in BalanCD/Hycell 1:1 mixture of media (P1-3, P1-4, P2-3, P2-4).

Example 5

Given our desire to develop feeds that will support higher density perfusion processes, this example contains experimental results from evaluating various feeds and feed combinations to identify those which would provide nutritional support for cultures exceeding 30 million cells per milliliter, preferably supporting perfusion runs at 50 million cells per milliliters of culture. Cultures were inoculated at 40 million cells per milliliter into the BalanCD/Hycell base medium reported in Example 4 above, supplemented with CHOZN (10%) and Feed1 (10%). One of the cultures was additionally supplemented with 7.5% cottonseed hydrolyzate. Media composition is provided below.

Example 5 Medium 1

| Feed Component | Concentration |
| --- | --- |
| BalanCD/Hycell | 1:1 |
| CHOZN | 10% |
| FEED 1 | 10% |
| L-Glutamine | 8 mM |
| Galactose | 10 mM |

Example 5 Medium 2

| Feed Component | Concentration |
| --- | --- |
| BalanCD/Hycell | 1:1 |
| CHOZN | 10% |
| FEED 1 | 10% |
| L-Glutamine | 8 mM |
| Galactose | 10 mM |
| Cotton seed hydrolysate | 7.5% |

The Example 5 Formulations were tested in batch mode using culture longevity as the end point. Cultures were maintained at 33.5° C. without additional feeding until the viability declined to ~80%. Viable cell density and viability of culture are shown in FIGS. 22A and 22B, respectively.

Figures 22A, 22B:
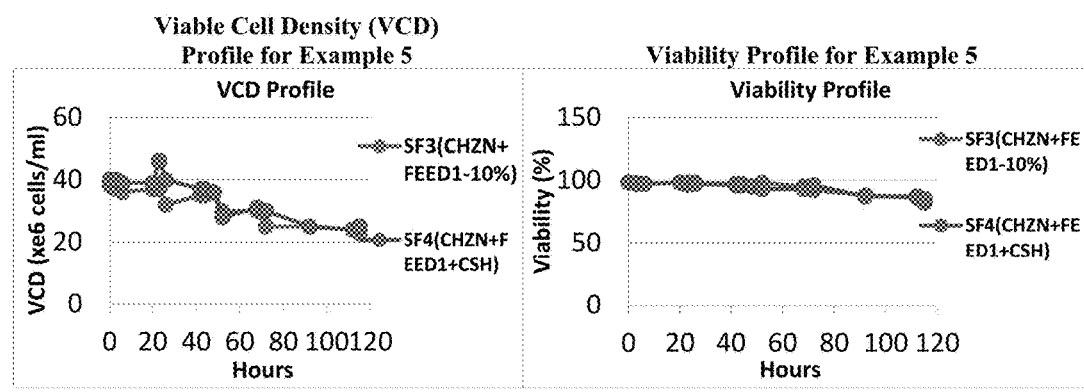
FIG. 22A is a chart of culture viable cell density (VCD) for media formulations of Example 5.
FIG. 22B is a chart of viability for media formulations of Example 5.

FIGS. 22A and 22B depict viable cell density (VCD) and viability profile of cultures maintained in two different media formulations of the BalanCD/Hycell 1:1 mixture base medium. Both feed formulations resulted in batch culture longevity of 4 days (Any reduction of cell density was due to intensive sampling from small volume cultures and attachment of cells cultivated in high density culture to the pipette)

This Example 5 demonstrates that the BalanCD/Hycell media formulations described here are rich enough to support high density perfusion runs, and further, that the perfusion rate may perhaps be reduced due to decreased risk of nutrient depletion.

Example 6

Exploring further performance of media formulations described in Example 5 on product quality in simulated perfusion mode cultures were set up at 40-50 million cells per milliliter in BalanCD/Hycell base medium supplemented with 10% CHOZN, 10% Feed1, 10 mM Galactose and 7.5% cotton seed hydrolysate. Additionally two of the three cultures were supplemented with 0.8 uM dexamethasone and 20 mM ManNac. One of these two cultures received 0.01 uM magnesium chloride. Media composition is provided in Example 6 Medium 1-3 (see tables below).

Example 6 Medium 1

| Feed Component | Concentration |
| --- | --- |
| BalanCD/Hycell | 1:1 |
| CHOZN | 10% |
| FEED 1 | 10% |
| L-Glutamine | 8 mM |
| Galactose | 10 mM |
| Cotton seed hydrolysate | 7.5% |

Example 6 Medium 2

| Feed Component | Concentration |
| --- | --- |
| BalanCD/Hycell | 1:1 |
| CHOZN | 10% |
| FEED 1 | 10% |
| L-Glutamine | 8 mM |
| Galactose | 10 mM |
| Cotton seed hydrolysate | 7.5% |
| Dexamethasone | 0.8 uM |
| ManNac | 20 mM |

Example 6 Medium 3

| Feed Component | Concentration |
| --- | --- |
| BalanCD/Hycell | 1:1 |
| CHOZN | 10% |
| FEED 1 | 10% |
| L-Glutamine | 8 mM |
| Galactose | 10 mM |
| Cotton seed hydrolysate | 7.5% |
| Dexamethasone | 0.8 uM |
| ManNAc | 20 mM |
| Magnesium chloride | 0.01 uM |

Cultures were cultivated at 33.5° C. Perfusion was carried out by performing medium exchange every 24 hours.

Samples were analyzed with respect to growth (viable cell density and viability), titers and isoform profile using IEF gels. Culture viable cell density (VCD) and viability are shown in FIGS. 23A and 23B, respectively while isoform profile correlating with the level of sialic acid content is shown in FIG. 24 (the IEF Gel for this Example).

Figure 23A:
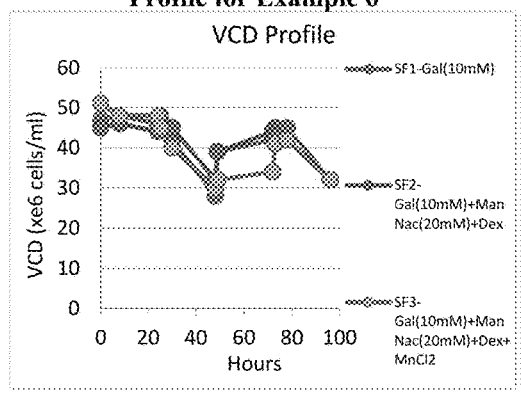
FIG. 23A is a chart of culture viable cell density (VCD) for media formulations of Example 6.
Figure 23B:
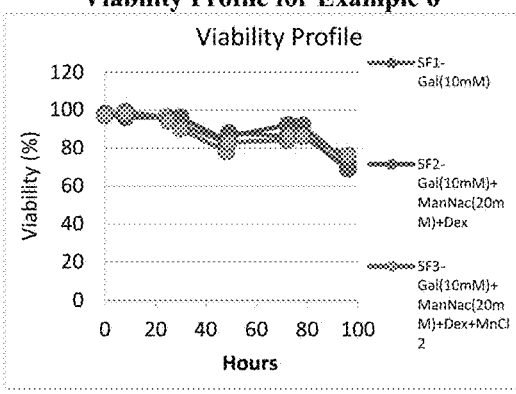
FIG. 23B is a chart of viability for media formulations of Example 6.

FIGS. 23A and 23B show viable cell density (VCD) and viability profile of cultures maintained in three different media formulations of the BalanCD/Hycell base medium. All feed formulations were tested for 5 days with four medium exchanges performed every 24 hours. Decrease in cell density at later stage of the cultures was the result of heavy sample testing and cells attaching to the pipette.

Figure 24:
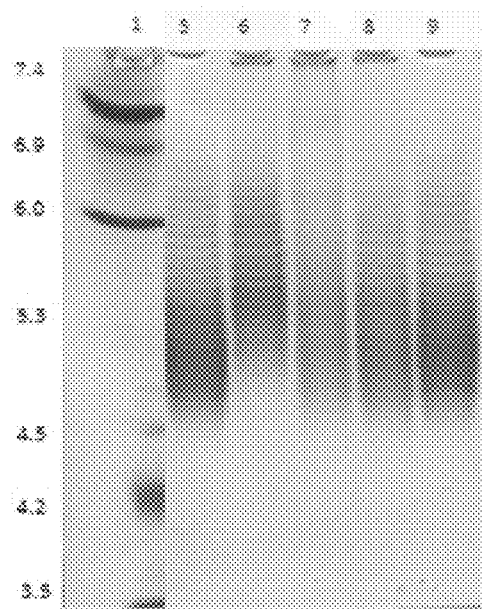
FIG. 24 is a photograph of isoelectrofocusing (IEF) Gel for media formulations of Example 6.

FIG. 24 shows the isoform profile of samples from harvest culture (day 4, fourth medium exchange) composed of Medium 1 (lane 6), Medium 2 (lane 7) and Medium 3 (lane 8). Lanes 5 and 9 correspond to reference standard.

Data generated from experiments described in Example 6 indicates that despite similar culture performance with respect to viability and viable cell density, the product quality is further improved by formulation of Medium 2 and Medium 3.

Example 7

In yet a further example of high density cultures tested in a perfusion process involving repetitive medium exchanges at predetermined time intervals, we inoculated cells at 40-50 million cells per milliliter into four different BalanCD/Hycell 1:1 mixtures. Mixture 1 was supplemented with Ex-Cell CHOZN Platform Feed and BalanCD Feed1, Mixture 2 was supplemented with Ex-Cell CHOZN Platform Feed, BalanCD Feed1 and BalanCD Feed2; Mixture 3 was supplemented with Ex-Cell CHOZN Platform Feed and Efficient Feed A; and Mixture 4 was supplemented with Ex-Cell CHOZN Platform Feed, BalanCD Feed1, BalanCD Feed2 and Efficient Feed A. All four of the BalanCD/Hycell 1:1 mixtures contained additional supplementation of 8 mM L-glutamine, 10 mM galactose, 7.5% cotton seed hydrolysate, 0.8 uM dexamethasone, and 20 mM ManNAc.

Example 7—Medium 1

| Feed Component | Concentration |
| --- | --- |
| BalanCD/Hycell | 1:1 |
| CHOZN | 10% |
| FEED 1 | 10% |
| L-Glutamine | 8 mM |
| Galactose | 10 mM |
| Cotton seed hydrolysate | 7.5% |
| Dexamethasone | 0.8 uM |
| ManNAc | 20 mM |

Example 7—Medium 2

| Feed Component | Concentration |
| --- | --- |
| BalanCD/Hycell | 1:1 |
| CHOZN | 10% |
| FEED 1 | 5% |
| FEED 2 | 5% |
| L-Glutamine | 8 mM |
| Galactose | 10 mM |
| Cotton seed hydrolysate | 7.5% |
| Dexamethasone | 0.8 uM |
| ManNAc | 20 mM |

Example 7—Medium 3

| Feed Component | Concentration |
| --- | --- |
| BalanCD/Hycell | 1:1 |
| CHOZN | 10% |
| FEED 2 | 10% |
| L-Glutamine | 8 mM |
| Galactose | 10 mM |
| Cotton seed hydrolysate | 7.5% |
| Dexamethasone | 0.8 uM |
| ManNAc | 20 mM |

Example 7—Medium 4

| Feed Component | Concentration |
| --- | --- |
| BalanCD/Hycell | 1:1 |
| CHOZN | 10% |
| FEED 1 | 3% |
| FEED 2 | 3% |
| Efficient FEED A | 3% |
| L-Glutamine | 8 mM |
| Galactose | 10 mM |
| Cotton seed hydrolysate | 7.5% |
| Dexamethasone | 0.8 uM |
| ManNAc | 20 mM |

Cultures were maintained at 33.5° C. Perfusion conditions were achieved by replacing medium every 24 hours (for a total of five exchanges). Product quality was measured by IEF gel analysis during four consecutive medium exchanges (See FIG. 25).

Figure 25:
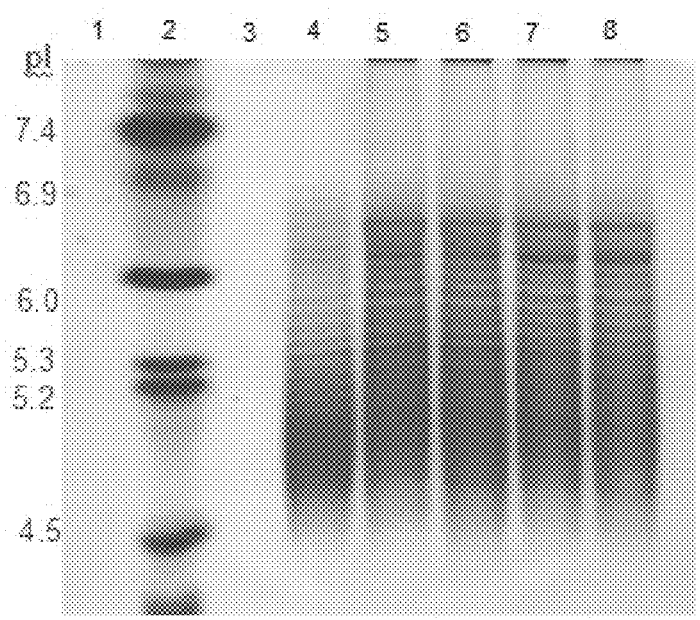
FIG. 25 is a photograph of isoelectrofocusing (IEF) Gel for media formulations of Example 7.

FIG. 25 shows samples form the last of the five medium exchanges (day 5): standard is lane 4; samples from Medium 1, Medium 2, Medium 3, Medium 4 (lanes 5-8, respectively). This data indicate that all four media formulations support high cell density perfusion with simulated perfusion rate of 1 bioreactor volume per day, and that these conditions allow for production of etanercept protein with sialic acid content resulting in the isoform distribution substantially similar to the reference standard (commercially available Enbrel®). In a perfusion mode where the steady medium flow delivers nutrients and removes wastes in a continuous fashion the product quality can be expected to improve even further.

What is claimed is:

1. A perfusion method for manufacturing correctly folded etanercept comprising the following steps: (a) preparing a mixture comprising cells capable of expressing a protein comprising etanercept and a culture medium suitable for conducting such expression; (b) in a suitable reaction vessel containing the mixture, causing the cells to produce the protein comprising etanercept; and (c) periodically or continuously removing spent culture medium from, and adding fresh culture medium to, the reaction vessel, wherein the protein comprising etanercept produced in the method comprises at least 40 wt. %, 50 wt. %, or 60 wt. % of correctly folded etanercept, and wherein the culture medium comprises a Chinese hamster ovary cell medium as a base feed medium and wherein the culture medium comprises dexamethasone, galactose and N-acetylmannosamine (ManNAc).

2. A perfusion method for manufacturing correctly folded etanercept comprising the following steps: (a) preparing a mixture comprising cells capable of expressing a protein comprising etanercept and a culture medium suitable for conducting such expression; (b) in a suitable reaction vessel containing the mixture, causing the cells to produce the protein comprising etanercept; and (c) periodically or continuously removing spent culture medium from, and adding fresh culture medium to, the reaction vessel;
and wherein:
(1) the culture medium comprises a Chinese hamster ovary cell medium, dexamethasone, galactose and N-acetylmannosamine (ManNAc);
(2) prior to step (a), the cells capable of expressing the protein comprising etanercept are grown in a growth phase at a temperature of 28° C. to 37° C.;
(3) production of the protein comprising etanercept is carried out at a temperature of 33° C. to 36° C.; and
(4) the protein comprising etanercept comprises at least 40 wt. %, 50 wt. %, or 60 wt. % of correctly folded etanercept, and wherein the total amount of correctly folded and incorrectly folded protein is produced at a titer of about 0.2 to about 1 g/L.

3. The perfusion method of claim 2 wherein the production of the protein comprising etanercept is conducted at 33° C. to 34° C., and the amount of correctly folded etanercept is at least 60 wt. %.

4. The perfusion method of claim 2 in which an alternating tangential flow cell retention device is used to recirculate medium containing waste products and the protein comprising etanercept past a hollow fiber filter whereby the waste products and the protein comprising etanercept are removed from the reaction vessel.

5. The perfusion method of claim 2 wherein the culture medium further comprises at least one feed supplement selected from glutamine and cottonseed hydrolysate.

6. The perfusion method of claim 5 wherein the culture medium comprises cottonseed hydrolysate.

7. A perfusion method for producing correctly folded etanercept said method comprising the steps of: (a) preparing a mixture comprising cells capable of expressing a protein comprising etanercept and a culture medium suitable for conducting such expression; (b) in a suitable reaction vessel containing the mixture, causing the cells to produce the protein comprising etanercept; and (c) periodically or continuously removing spent culture medium from, and adding fresh culture medium to, the reaction vessel; wherein dexamethasone, galactose and N-acetylmannosamine (ManNAc) are present in the culture medium.

8. The perfusion method of claim 7 wherein
(1) prior to step (a), the cells capable of expressing the protein comprising etanercept are grown in a growth phase at a temperature selected from (i) about 28° C. to about 37° C.; and (ii) about 35° C. to about 36° C.; and
(2) production of the protein comprising etanercept is carried out at a temperature selected from (i) greater than about 32° C.; (ii) greater than about 33° C.; (iii) greater than about 34° C.; (iv) greater than about 35° C.; (v) the range of about 33° C. to about 36° C.; (vi) the range of about 35° C. to about 36° C.; (vii) 32.5° C.; (viii) 33.5° C.; (ix) 34.5° C.; and (x) 35.5° C.

9. The method of claim 8 wherein the protein comprising etanercept produced in the method comprises at least 40 wt. %, 50 wt. %, or 60 wt. % of correctly folded etanercept; the culture medium comprises a Chinese hamster ovary cell base medium, glutamine and cottonseed hydrolysate; and correctly folded and incorrectly folded protein is produced at a titer of about 0.2 to about 1 g/L.

10. A perfusion method for producing correctly folded etanercept, said method comprising the steps of: (a) preparing a mixture comprising cells capable of expressing a protein comprising etanercept and a culture medium suitable for conducting such expression; (b) in a suitable reaction vessel containing the mixture, causing the cells to produce the protein comprising etanercept; and (c) periodically or continuously removing spent culture medium from, and adding fresh culture medium to, the reaction vessel; wherein:
(i) dexamethasone, galactose and N-acetylmannosamine (ManNAc) are present in the culture medium and
(ii) the culture medium comprises feed media comprising a Chinese hamster ovary cell medium, glutamine and cottonseed hydrolysate, and correctly folded and incorrectly folded protein is produced at titer of about 0.2 to about 1 g/L; and
(iii) production of the protein comprising etanercept is carried out at a temperature selected from (i) greater than about 32° C.; (ii) greater than about 33° C.; (iii) greater than about 34° C.; (iv) greater than about 35° C.; (v) the range of about 33° C. to about 36° C.; (vi) the range of about 35° C. to about 36° C.; (vii) 32.5° C.; (viii) 33.5° C.; (ix) 34.5° C.; and (x) 35.5° C.

11. The method of claim 10 wherein the production of the protein comprising etanercept is carried out at a temperature of 33° C. to 36° C., and the protein comprising etanercept comprises at least 60 wt. % correctly folded etanercept.

12. The method of claim 11 wherein the production of the protein comprising etanercept is carried out at a temperature of 33° C. to 34° C.

13. A perfusion method for manufacturing correctly folded etanercept comprising the following steps: (a) preparing a mixture comprising cells capable of expressing a protein comprising etanercept and a culture medium suitable for conducting such expression; (b) in a suitable reaction vessel containing the mixture, causing the cells to produce the protein comprising etanercept; and (c) periodically or continuously removing spent culture medium from, and adding fresh culture medium to, the reaction vessel; wherein (i) step (b) is carried out at or above 33° C.; (ii) the culture medium comprises at least one of dexamethasone, galactose, glutamine, cottonseed hydrolysate, and N-acetylmannosamine (ManNAc); (iii) the protein comprising etanercept comprises at least 60 wt. % correctly folded etanercept; and (iv) the protein comprising etanercept is produced at a titer of about 0.2 to about 1 g/L.

14. The perfusion method of claim 13 wherein the culture medium comprises dexamethasone, galactose and ManNAc.

15. The perfusion method of claim 14 wherein the culture medium comprises a Chinese hamster ovary cell medium.

16. A perfusion method for manufacturing correctly folded etanercept comprising the following steps: (a) preparing a mixture comprising cells capable of expressing a protein comprising etanercept and a culture medium suitable for conducting such expression; (b) in a suitable reaction vessel containing the mixture, causing the cells to produce the protein comprising etanercept; and (c) periodically or continuously removing spent culture medium from, and adding fresh culture medium to, the reaction vessel, wherein the protein comprising etanercept produced in the method comprises at least 40 wt. %, 50 wt. %, or 60 wt. % of correctly folded etanercept, wherein the culture medium comprises a Chinese hamster ovary cell medium as a base feed medium and wherein the culture medium comprises cottonseed hydrolysate.

* * * * *